United States Patent
Kurihara et al.

(10) Patent No.: US 9,150,895 B2
(45) Date of Patent: Oct. 6, 2015

(54) MANUFACTURING METHOD FOR SUGAR SOLUTION AND DEVICE FOR SAME

(75) Inventors: Hiroyuki Kurihara, Kamakura (JP); Atsushi Minamino, Kamakura (JP); Yuki Yamamoto, Kamakura (JP); Katsushige Yamada, Kamakura (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 13/634,933

(22) PCT Filed: Mar. 14, 2011

(86) PCT No.: PCT/JP2011/055902
§ 371 (c)(1),
(2), (4) Date: Nov. 8, 2012

(87) PCT Pub. No.: WO2011/115039
PCT Pub. Date: Sep. 22, 2011

(65) Prior Publication Data
US 2013/0059345 A1    Mar. 7, 2013

(30) Foreign Application Priority Data
Mar. 15, 2010    (JP) .................. 2010-057403

(51) Int. Cl.
*C12P 19/14*  (2006.01)
*C12P 19/02*  (2006.01)
*C13K 1/02*   (2006.01)
*C13K 13/00*  (2006.01)

(52) U.S. Cl.
CPC .................. *C12P 19/14* (2013.01); *C12P 19/02* (2013.01); *C13K 1/02* (2013.01); *C13K 13/002* (2013.01)

(58) Field of Classification Search
CPC ............ C12P 19/00; C12P 19/14; C12P 7/56; C12P 7/06; C12M 29/04
USPC .......................... 435/99, 139, 161, 72, 297.1
See application file for complete search history.

(56) References Cited

U.S. PATENT DOCUMENTS 4,713,334 A * 12/1987 Fujishima et al. .............. 435/99
7,189,306 B2 * 3/2007 Gervais .......................... 162/21

FOREIGN PATENT DOCUMENTS

CN    1451755 A     10/2003
CN    101434977 A   5/2009

(Continued)

OTHER PUBLICATIONS

Hamada H et al. Effect of Additives on Protein Aggregation. 2009. Current Pharmaceutical Biotechnology. 10, pp. 400-407.*

(Continued)

*Primary Examiner* — David J Steadman
*Assistant Examiner* — Paul Holland
(74) *Attorney, Agent, or Firm* — DLA Piper LLP (US)

(57) ABSTRACT

A method of hydrolysis of cellulose uses a filamentous fungus-derived cellulase as a carbohydrase and includes adding the carbohydrase to cellulose to perform primary hydrolysis and then subjecting the primary hydrolysate to solid-liquid separation into a primary sugar liquid and solids; adding water to the solids and performing secondary hydrolysis, followed by subjecting the secondary hydrolysate to solid-liquid separation into a secondary sugar liquid and a residue; and filtering the primary sugar liquid and/or secondary sugar liquid through an ultrafiltration membrane, and recovering the carbohydrase from the feed side and recovering a sugar solution from the permeate side.

12 Claims, 14 Drawing Sheets

(56) References Cited

FOREIGN PATENT DOCUMENTS

| | | | |
|---|---|---|---|
| JP | 55-144885 | A | 11/1980 |
| JP | 59-213396 | A | 12/1984 |
| JP | 63-087994 | A | 4/1988 |
| JP | 63-137691 | A | 6/1988 |
| JP | 11-506934 | A | 6/1999 |
| JP | 3041380 | B2 | 5/2000 |
| JP | 2001-095597 | A | 4/2001 |
| JP | 2003-212888 | A | 7/2003 |
| JP | 2005-229821 | A | 9/2005 |
| JP | 2006-087319 | A | 4/2006 |
| JP | 2008-161125 | A | 7/2008 |
| JP | 2008-206484 | A | 9/2008 |
| JP | 2008-535664 | A | 9/2008 |
| JP | 2011-019483 | A | 2/2011 |

OTHER PUBLICATIONS

Liu S et al. Membrane Filtration: Concentration and Purification of Hydrolyzates from Biomass. 2008. Journal of Biobased Materials and Bioenergy. vol. 2. pp. 121-134.*

Ramos LP et al. Enzyme Recycling During Fed-Batch Hydrolysis of Cellulose Derived from Steam-Exploded *Eucalyptus viminalis*. 1994. Applied Biochemistry and Biotechnology. vol. 45/46. pp. 193-207.*

Rosgaard L et al. Evaluation of Minimal *Trichoderma reesei* Cellulase Mixtures on Differently Pretreated Barley Straw Substrates. 2007. Biotechnology Progress. 23, pp. 1270-1276.*

A. Aden et al., "Lignocellulosic Biomass to Ethanol Process Design and Economics Utilizing Co-Current Dilute Acid Prehydrolysis and Enzymatic Hydrolysis for Corn Stover," NREL Technical Report, 2002 (Abstract).

* cited by examiner

MANUFACTURING METHOD FOR SUGAR SOLUTION AND DEVICE FOR SAME

RELATED APPLICATIONS

This is a §371 of International Application No. PCT/JP2011/055902, with an international filing date of Mar. 14, 2011 (WO 2011/115039 A1, published Sep. 22, 2011), which is based on Japanese Patent Application No. 2010-057403, filed Mar. 15, 2010, the subject matter of which is incorporated by reference.

TECHNICAL FIELD

This disclosure relates to a method for producing a sugar liquid from cellulose, and an apparatus for the method.

BACKGROUND

Processes of fermentation production of chemical products using sugars as raw materials have been used for producing various industrial materials. At present, as the sugars to be used as fermentation feedstocks, those derived from food materials such as sugar cane, starch and sugar beet are industrially used. However, in view of the fact that rise in the prices of food materials due to future increase in the world population is expected, or in an ethical view of the fact that sugars as industrial materials may compete with sugars for food, a process for efficiently producing a sugar liquid from a renewable nonfood resource, that is, a cellulose-containing biomass, or a process for using an obtained sugar liquid as a fermentation feedstock to efficiently convert the sugar liquid to an industrial material needs to be constructed in the future.

Examples of disclosed methods for producing a sugar liquid from a cellulose-containing biomass include methods for producing sugar liquids by acid hydrolysis of cellulose and hemicellulose using concentrated sulfuric acid (Japanese Translated PCT Patent Application Laid-open No. 11-506934 and JP 2005-229821 A) and a method wherein a cellulose-containing biomass is subjected to hydrolysis treatment using dilute sulfuric acid and then enzymatically treated with cellulase or the like to produce a sugar liquid (A. Aden et al., "Lignocellulosic Biomass to Ethanol Process Design and Economics Utilizing Co-Current Dilute Acid Prehydrolysis and Enzymatic Hydrolysis for Corn Stover," NREL Technical Report (2002)). Further, examples of disclosed methods using no acid include a method wherein a cellulose-containing biomass is hydrolyzed using subcritical water at about 250° C. to 500° C. to produce a sugar liquid (JP 2003-212888 A), a method wherein a cellulose-containing biomass is subjected to subcritical water treatment and then enzymatically treated to produce a sugar liquid (JP 2001-95598 A), and a method wherein a cellulose-containing biomass is subjected to hydrolysis treatment with pressurized hot water at 240° C. to 280° C. and then enzymatically treated to produce a sugar liquid (JP 3041380 B).

In recent years, methods of hydrolysis of a biomass which use less energy and cause less environmental load, but produce sugar at high yields have been extensively studied. However, such methods using enzymes have a drawback in that the costs of enzymes are high.

To solve these technical problems, methods of recovering and reusing the enzymes used in the hydrolysis have been proposed. Examples of such methods include a method wherein continuous solid-liquid separation is carried out with a spin filter and the obtained sugar liquid is filtered through an ultrafiltration membrane to recover the enzymes (JP 2006-87319 A), a method wherein a surfactant is fed at the stage of enzymatic saccharification to suppress enzyme adsorption and thereby enhance the recovery efficiency (JP 63-87994 A), a method wherein the residue produced by enzymatic saccharification is subjected to electric treatment to recover the enzyme component (JP 2008-206484 A) and a method wherein the residue produced by enzymatic saccharification is fed again to another batch of biomass and the enzymes is thereby reused (JP 55-144885 A).

Methods for producing sugar liquids by recovering/reusing enzyme have been developed as described above, but the effects of these methods have been insufficient in view of reduction in the amount of the enzyme used. Therefore, it could be helpful to provide a process wherein the effect of reducing the amount of enzyme is higher than those in the conventional methods.

SUMMARY

We discovered a method of hydrolysis of cellulose using a filamentous fungus-derived cellulase as a carbohydrase, which method comprises: adding the carbohydrase to cellulose to perform primary hydrolysis and then subjecting the primary hydrolysate to solid-liquid separation into a primary sugar liquid and solids; adding water to the solids and performing secondary hydrolysis, followed by subjecting the secondary hydrolysate to solid-liquid separation into a secondary sugar liquid and a residue; and filtering the primary sugar liquid and/or secondary sugar liquid through an ultrafiltration membrane and recovering the carbohydrase from the feed side and recovering a sugar solution from the permeate side.

We thus provide (1) to (13):

(1) A method for producing a sugar liquid by using as a carbohydrase a filamentous fungus-derived cellulase to hydrolyze cellulose, the method comprising:
  adding said carbohydrase to cellulose to perform primary hydrolysis and then subjecting the primary hydrolysate to solid-liquid separation into a primary sugar liquid and solids;
  adding water to the solids and performing secondary hydrolysis, followed by subjecting the secondary hydrolysate to solid-liquid separation into a secondary sugar liquid and a residue; and
  filtering the primary sugar liquid and/or secondary sugar liquid through an ultrafiltration membrane, and recovering the carbohydrase from the feed side and recovering a sugar liquid from the permeate side.

(2) The method for producing a sugar liquid according to (1), wherein the filamentous fungus-derived cellulase is *Trichoderma*-derived cellulase.

(3) The method for producing a sugar liquid according to (1) or (2), wherein the cellulose is derived from a processed product prepared by ammonia treatment, hydrothermal treatment or dilute sulfuric acid treatment of biomass.

(4) The method for producing a sugar liquid according to any of (1) to (3), wherein the secondary hydrolysis is hydrolysis in the presence of one or more selected from the group consisting of inorganic salts (excluding calcium salts), hydrophilic organic solvents, amino acids and nonionic surfactants, and sugar liquids comprising these substances, (5) The method for producing a sugar liquid according to (4), wherein the inorganic salt(s) (excluding calcium salts) is/are one or more selected from the group consisting of sodium salts, potassium salts, magnesium salts, sulfuric acid salts, ammonium salts, hydrochloric acid salts, phosphoric acid salts, acetic acid salts and nitric acid salts.

(6) The method for producing a sugar liquid according to (5), wherein the inorganic salt(s) (excluding calcium salts) is/are one or more selected from the group consisting of sodium chloride, sodium acetate, sodium sulfate, sodium hydrogen sulfate, sodium dihydrogen phosphate, sodium hydrogen phosphate, potassium chloride, ammonium chloride, dipotassium hydrogen phosphate, ammonium sulfate, magnesium chloride and magnesium sulfate.

(7) The method for producing a sugar liquid according to (4), wherein the hydrophilic organic solvent(s) is/are one or more selected from the group consisting of methanol, ethanol, 1-propanol, isopropanol, N,N-dimethylformamide, butanol, acetone, acetonitrile, ethylene glycol and glycerin.

(8) The method for producing a sugar liquid according to (4), wherein the amino acid(s) is/are one or more selected from the group consisting of arginine, cysteine, glutamic acid, histidine and lysine.

(9) The method for producing a sugar liquid according to any of (1) to (8), wherein the solid-liquid separation of a primary hydrolysate and/or secondary hydrolysate is press filtration.

(10) The method for producing a sugar liquid according to any of (1) to (9), the method comprising the step of filtering the sugar liquid through a reverse osmosis membrane and/or nanofiltration membrane to concentrate the sugar liquid.

(11) An apparatus for the method for producing a sugar liquid according to any of (1) to (10), the apparatus comprising as constituents a stirring tank for primary hydrolysis; solid-liquid separation device; secondary hydrolysis tank or press filtration device for secondary hydrolysis; solid-liquid separation device(s) for the primary hydrolysate and/or secondary hydrolysate; and ultrafiltration membrane device for separating the carbohydrase and the sugar liquid from the primary sugar liquid and/or the secondary sugar liquid.

(12) An apparatus for the method for producing a sugar liquid according to any of (1) to (10), the apparatus comprising as constituents a reaction vessel for primary hydrolysis; press filtration device having a warm-water supply tank; circulation line for circulating the filtrate from the press filtration device to the warm-water supply tank; and ultrafiltration membrane device for separating the carbohydrase and the sugar liquid from the primary sugar liquid and/or the secondary sugar liquid.

(13) The apparatus according to (11) or (12), comprising as a constituent a sugar liquid concentrating device equipped with a reverse osmosis membrane and/or a nanofiltration membrane for concentrating the sugar liquid obtained with the ultrafiltration membrane device.

Primary hydrolysis is followed by solid-liquid separation, and the residual enzyme components contained in the obtained solids are used to perform secondary hydrolysis. This produces 1) an effect to increase the sugar yield and 2) an effect to increase the recovered amount of enzyme. Therefore, our methods are economically advantageous over conventional techniques.

DESCRIPTION OF SYMBOLS

Figure 1:
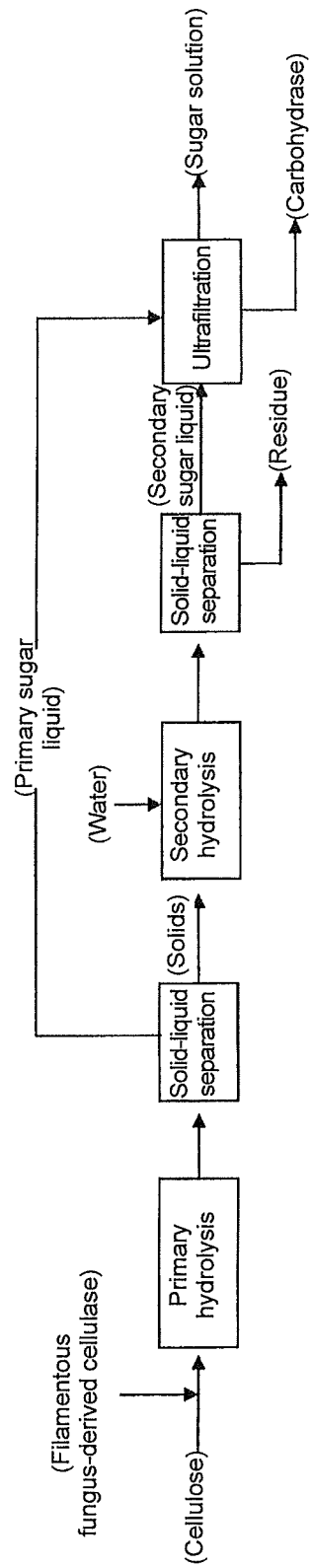
FIG. 1 is a schematic diagram showing an example of our method for producing a sugar liquid.

1 Thermostat
2 Stirring tank
3 Cellulose inlet
4 Stirring device
5 Water supply line
6 Warm-water supply tank
7 Warm-water supply tank thermostat
8 Press filtration device
9 Compressor
10 Circulation line
11 Filtrate recovery tank 12 Ultrafiltration membrane device
13 Carbohydrase recovery line
14 Hydrolysate inlet
15 Warm-water inlet
16 Outer frame
17 Filter cloth
18 Solids (primary hydrolysate)
19 Pressing plate
20 Inside of press filtration chamber
21 Hydrolysate-inlet-cum-warm-water inlet
22 Sugar solution tank
23 Nanofiltration membrane device or reverse osmosis membrane device
24 Filtrate line
25 Solid-liquid separation device
26 Solid transfer means
27 Thermostat 2 (secondary hydrolysis tank)
28 Secondary hydrolysis tank
29 Stirring device 2 (secondary hydrolysis tank)
30 Solid-liquid separation device 2 (secondary hydrolysate)
31 Secondary sugar liquid tank
32 Secondary sugar liquid recovery tank
33 Secondary sugar liquid ultrafiltration membrane device
34 Secondary sugar liquid transfer line
35 Transfer line
36 Microfiltration membrane device
37 Microfiltration membrane raw liquid tank
38 Microfiltration membrane
39 Compressed-air supply device
40 Reverse-washing pump
41 Microfiltrate recovery tank

DETAILED DESCRIPTION

Large amounts of celluloses are contained in herbaceous biomasses such as bagasse, switchgrass, napier grass, *Erianthus*, corn stover, rice straw and wheat straw; and woody biomasses such as trees and waste building materials. These cellulose-containing biomasses can be preferably used as raw materials.

Cellulose-containing biomass contains, in addition to cellulose and hemicellulose (hereinafter referred to as "cellulose" as a general term for cellulose and hemicellulose), lignin and the like which are aromatic macromolecules. Therefore, in cases where cellulose derived from a biomass is used as a raw material for a sugar liquid in the method for producing a sugar liquid, the efficiency of enzymatic hydrolysis can be enhanced by pretreatment. Examples of the method of pretreatment of a cellulose-containing biomass include acid treatment, sulfuric acid treatment, dilute sulfuric acid treatment, alkaline treatment, caustic soda treatment, ammonia treatment, hydrothermal treatment, subcritical water treatment, pulverization treatment and steaming treatment. The method of pretreatment is preferably ammonia treatment, hydrothermal treatment or dilute sulfuric acid treatment.

The ammonia treatment is carried out according to JP 2008-161125 A and JP 2008-535664A. For example, ammonia is added to the biomass at a concentration within the range of 0.1 to 15% by weight, and the treatment is carried out at 4 to 200° C., preferably 90 to 150° C. The ammonia to be added may be in the state of either liquid or gas. Further, the form of the ammonia to be added may be either pure ammonia or aqueous ammonia. The number of times of the treatment is not restricted, and 1 or more times of the treatment may be carried out. In particular, in cases where the treatment is carried out 2 or more times, the conditions for the first treatment may be different from those for the second and later treatments. The treated product obtained by the ammonia treatment needs to be subjected to neutralization of ammonia or removal of ammonia to further carry out enzymatic hydrolysis reaction. The neutralization of ammonia may be carried out either after removal of the solids from the hydrolysate by solid-liquid separation or in the state in which the solids are contained. The acid reagent to be used for the neutralization is not restricted. The ammonia can be removed by maintaining the ammonia-treated product under reduced pressure to allow evaporation of the ammonia into the state of gas. The removed ammonia may be recovered and reused.

In the case of dilute sulfuric acid treatment, the concentration of sulfuric acid is preferably 0.1 to 15% by weight, more preferably 0.5 to 5% by weight. The reaction temperature may be set within the range of 100 to 300° C., and is preferably set within the range of 120 to 250° C. The reaction time may be set within the range of 1 second to 60 minutes. The number of times of the treatment is not restricted, and one or more times of the treatment may be carried out. In particular, in cases where the treatment is carried out two or more times, the conditions for the first treatment may be different from those for the second and later treatments. Since the hydrolysate obtained by the dilute sulfuric acid treatment contains acid, neutralization is necessary to further carry out hydrolysis reaction with cellulase or to use the hydrolysate as a fermentation feedstock.

In the case of hydrothermal treatment, water is added such that the cellulose-containing biomass is contained at 0.1 to 50% by weight, and the treatment is then carried out at a temperature of 100 to 400° C. for 1 second to 60 minutes. By performing the treatment under such temperature conditions, hydrolysis of cellulose occurs. The number of times of the treatment is not restricted, and one or more times of the treatment may be carried out. In particular, in cases where the treatment is carried out two or more times, the conditions for the first treatment may be different from those for the second and later treatments.

The cellulase is filamentous fungus-derived cellulase. Examples of the filamentous fungus include microorganisms such as *Trichoderma, Aspergillus, Cellulomonas, Clostridium, Streptomyces, Humicola, Acremonium, Irpex, Mucor* and *Talaromyces*. Since these microorganisms secrete cellulase into the culture medium, the culture medium may be used as it is as unpurified filamentous fungus-derived cellulase, or the culture medium may be purified and formulated to be used as a mixture containing filamentous fungus-derived cellulase. In cases where the filamentous fungus-derived cellulase is used as a purified and formulated product, a substance(s) other than the enzyme, such as a protease inhibitor, dispersant, solubilizer and/or stabilizer may be added to prepare the cellulase formulation.

The filamentous fungus-derived cellulase is preferably cellulase produced by *Trichoderma* (hereinafter referred to as *Trichoderma*-derived cellulase). The *Trichoderma*-derived cellulase is preferably cellulase derived from *Trichoderma reesei*, and specific examples of preferred *Trichoderma* microorganisms from which the cellulase is to be derived include *Trichoderma reesei* QM9414, *Trichoderma reesei* QM9123, *Trichoderma reesei* RutC-30, *Trichoderma reesei* PC3-7, *Trichoderma reesei* CL-847, *Trichoderma reesei* MCG77, *Trichoderma reesei* MCG80 and *Trichoderma viride* QM9123 (*Trichoderma viride* QM9123). The cellulase may also be derived from a mutant strain originated from the above-described *Trichoderma* microorganism, which mutant strain was prepared by mutagenesis using a mutagen, UV irradiation or the like to enhance the cellulase productivity.

Filamentous fungus-derived cellulase is an enzyme composition comprising a plurality of enzyme components such as cellobiohydrolase, endoglucanase, exoglucanase, β-glucosidase, xylanase and xylosidase, which enzyme composition has an activity to hydrolyze and saccharify cellulose. Since filamentous fungus-derived cellulase comprises such a plurality of enzyme components and allows, in cellulose degradation, efficient hydrolysis of cellulose due to their concerted effect or complementary effect, filamentous fungus-derived cellulase is preferably used.

Cellobiohydrolase is a general term for cellulases that hydrolyze cellulose from the terminal portions. The group of enzymes belonging to cellobiohydrolase are described as EC number: EC 3.2.1.91.

Endoglucanase is a general term for cellulases that hydrolyze cellulose molecular chains from their central portions. The group of enzymes belonging to endoglucanase are described as EC number: EC 3.2.1.4.

Exoglucanase is a general term for cellulases that hydrolyze cellulose molecular chains from their terminal portions. The group of enzymes belonging to exoglucanase are described as EC number: EC 3.2.1.74.

β-glucosidase is a general term for cellulases that acts on cellooligosaccharides or cellobiose. The group of enzymes belonging to β-glucosidase are described as EC number: EC 3.2.1.21.

Xylanase is a general term for cellulases that acts on hemicellulose or especially xylan. The group of enzymes belonging to xylanase are described as EC number: EC 3.2.1.8.

Xylosidase is a general term for cellulases that acts on xylooligosaccharides. The group of enzymes belonging to xylosidase are described as EC number: EC 3.2.1.37.

Such filamentous fungus-derived cellulase components can be separated by a known method such as gel filtration, ion exchange or two-dimensional electrophoresis, and the separated components can be subjected to amino acid sequence analysis (N-terminal analysis, C-terminal analysis or mass spectrometry), followed by comparison of the sequences with a database.

The enzyme activity of filamentous fungus-derived cellulase can be evaluated based on its hydrolytic activities on polysaccharides, such as the Avicel-degrading activity, carboxymethyl cellulose (CMC)-degrading activity, cellobiose-degrading activity, xylan-degrading activity and mannan-degrading activity. The main cellulase components involved in the Avicel-degrading activity are cellobiohydrolase and exoglucanase, which degrade cellulose from its terminal portions. The main cellulase components involved in the xylan-degrading activity are xylanase and xylosidase. The main cellulase component involved in the cellobiose-degrading activity is β-glucosidase. The main cellulase components involved in the CMC-degrading activity are cellobiohydrolase, exoglucanase and endoglucanase. The term "main" herein is used to mean that the component(s) is/are involved in the degradation to the highest extent(s) although other enzyme components are also involved in the degradation.

As the filamentous fungus-derived cellulase, a crude enzyme product is preferably used. The crude enzyme product is derived from the culture supernatant obtained after culturing a microorganism belonging to a genus of filamentous fungus for an arbitrary period in a medium prepared such that the microorganism produces cellulase. The medium components to be used are not restricted, and a medium supplemented with cellulose to promote production of cellulase may be generally used. As a crude enzyme product, the culture liquid may be used as it is, or the culture supernatant processed only by removal of the filamentous fungus may be preferably used.

The weight ratios of enzyme components in the crude enzyme product are not restricted and, for example, culture liquid derived from *Trichoderma reesei* contains 50 to 95% by weight cellobiohydrolase, and also contains as other components endoglucanase, β-glucosidase and the like. Microorganisms belonging to *Trichoderma* produce strong cellulase components into the culture liquid, while the β-glucosidase activity in the culture liquid is low since β-glucosidase is retained in the cells or on the cell surfaces. Therefore, β-glucosidase from a different species or from the same species may be added to the crude enzyme product. As the β-glucosidase from a different species, β-glucosidase derived from *Aspergillus* may be preferably used. Examples of the β-glucosidase derived from *Aspergillus* include Novozyme 188, which is commercially available from Novozyme. The method of addition of β-glucosidase from a different species or from the same species to the crude enzyme product may be a method wherein a gene is introduced to a microorganism belonging to *Trichoderma* to perform genetic recombination of the microorganism such that β-glucosidase is produced into the culture liquid, and the microorganism belonging to *Trichoderma* is then cultured, followed by isolating the culture liquid.

Hydrolysis of cellulose with the filamentous fungus-derived cellulase is carried out in two steps, that is, primary hydrolysis and secondary hydrolysis. The steps are described below in order.

The primary hydrolysis means that carbohydrase is added to cellulose that has not been brought into contact with carbohydrase, to perform hydrolysis. The enzyme used for the primary hydrolysis may be either the later-mentioned fresh enzyme or recovered enzyme and, in view of reduction in the amount of the enzyme used, especially in the amount of fresh enzyme used, it is preferred to use a mixture of both the recovered enzyme and fresh enzyme.

The reaction temperature during the primary hydrolysis is preferably within the range of 40 to 60° C., and, especially in cases where *Trichoderma*-derived cellulase is used, the reaction temperature is more preferably within the range of 45 to 55° C.

The reaction time of the primary hydrolysis is preferably within the range of 2 hours to 200 hours. In cases where the reaction time is less than 2 hours, sugar yield is insufficient, which is not preferred. On the other hand, in cases where the reaction time is more than 200 hours, the enzyme activity decreases, which is not preferred since, in the later-mentioned secondary hydrolysis, sugar yield is insufficient and the enzyme cannot be recovered.

The pH during the primary hydrolysis is preferably within the range of 4.0 to 5.5. In cases where *Trichoderma*-derived cellulase is used as the filamentous fungus-derived cellulase, the optimum reaction pH is 5.0, but, especially in the case of primary hydrolysis, the pH changes during the hydrolysis. Therefore, it is preferred to perform the hydrolysis while maintaining a constant pH using an acid or alkali.

The primary hydrolysate contains a primary sugar liquid and solids, and the solids contain polysaccharide components such as undegraded cellulose and hemicellulose, and components that cannot be originally degraded with carbohydrase, such as lignin. Further, a relatively large amount of filamentous fungus-derived cellulase is adhered to the solids. Therefore, to perform the later-mentioned secondary hydrolysis using the polysaccharide components and filamentous fungus-derived cellulase contained in the solids obtained by the primary hydrolysate, the obtained solids are recovered by solid-liquid separation. Examples of the method of solid-liquid separation include centrifugation and press filtration and recovering the solids by press filtration is preferred.

A reason why press filtration is preferred for the solid-liquid separation is that 1) high yield of sugar liquid can be achieved. We thus achieve improvement of the sugar recovery and the enzyme recovery as compared to those in the conventional techniques. Therefore, the method of solid-liquid separation is preferably one with which larger amounts of sugar liquid components can be recovered at once. The recovery of sugar liquid components by the solid-liquid separation can be improved especially by increasing the amount of water to be added after the secondary hydrolysis. However, an increase in the amount of water to be added causes a decrease in the sugar concentration in the secondary sugar liquid, which is not preferred. Therefore, in view of suppressing the amount of water used, while achieving a high sugar recovery, the solid-liquid separation is preferably performed by press filtration. Another reason why press filtration is preferred is that 2) a clear filtrate can be obtained. The primary sugar liquid and/or secondary sugar liquid obtained by solid-liquid separation is/are filtered through an ultrafiltration membrane to recover enzyme components. The sugar liquid to be passed through the ultrafiltration membrane preferably contains only small amounts of solids and particulate components in view of prevention of membrane fouling, and, in the case of press filtration, the filtrate contains only small amounts of solids and particulate components and may therefore be preferably used.

The secondary hydrolysis means that the second hydrolysis is preformed for the solids obtained by the solid-liquid separation of the primary hydrolysate, using only the filamentous fungus-derived cellulase adsorbed on the solids. That is, in the secondary hydrolysis, hydrolysis of solids is performed only with the adsorbed enzyme, without further addition of carbohydrase.

In contrast to conventional techniques (wherein only primary hydrolysis is performed), our method is characterized in that secondary hydrolysis is performed without further addition of enzyme, to improve the sugar yield and/or the enzyme recovery rate. Production of sugar and/or recovery of enzyme can of course be done also in the conventional techniques, but, by performing the secondary hydrolysis, more sugar and enzyme can be recovered. A major reason for this is prevention of enzyme inhibition by removal of the produced sugar. The hydrolysate after the primary hydrolysis contains a large amount of sugar components. By performing solid-liquid separation to remove the sugars (glucose, xylose and oligosaccharides) produced by the hydrolysis and further adding water, the concentration of the produced sugars contained as solution components can be decreased. By this, inhibition of the enzyme by the products can be prevented, and the secondary hydrolysis can be sufficiently carried out with only the enzyme adsorbed on the solids. Therefore, even with the same amount of enzyme used as that in a conventional technique, more sugar and/or enzyme can be recovered by performing the secondary hydrolysis.

The amount of water to be added is not restricted, and the addition is preferably carried out such that the solid concentration before the secondary hydrolysis is between 1% by weight and 20% by weight. In cases where the solid concentration is higher than 20% by weight, and in cases where the solid concentration is lower than 1% by weight, the yield of sugar and/or the recovered amount of enzyme may be low, which is inefficient and not preferred.

The reaction temperature during the secondary hydrolysis is preferably within the range of 40 to 60° C., and, especially in cases where *Trichoderma*-derived cellulase is used, the reaction temperature is more preferably within the range of 40 to 55° C., still more preferably 50° C.

The reaction time of the secondary hydrolysis is preferably within the range of 5 to 180 minutes. In cases where the reaction time is less than 5 minutes, the recovery efficiency of the adsorbed enzyme is low, while even in cases where the reaction is carried out for not less than 180 minutes, the recovery efficiency of the adsorbed enzyme does not increase, which is inefficient.

The pH during the secondary hydrolysis is preferably within the range of 6.0 to 8.0. In cases where *Trichoderma*-derived cellulase is used as the filamentous fungus-derived cellulase, the optimum reaction pH is 5.0 and, especially in the case of primary hydrolysis, the reaction is preferably performed at a pH of 5.0. On the other hand, in the secondary hydrolysis, since the main purpose is recovery of the adsorbed enzyme, the reaction is preferably carried out at a pH within the range of 6.0 to 8.0, in which the recovery efficiency of the adsorbed enzyme is high. At a pH of less than 6.0, the amount of recovery of enzyme decreases, while with a pH higher than 8.0, carbohydrase is deactivated, which is not preferred. That is, at a pH within the range of 6.0 to 8.0, the degree of deactivation of carbohydrase is extremely low and the recovery efficiency of carbohydrase can be high.

The secondary hydrolysate contains a secondary sugar liquid and solids and, similarly to the case of the primary hydrolysis, these can be separated from each other by solid-liquid separation, preferably press filtration.

In the secondary hydrolysis, one or more compounds selected from nonionic surfactants, amino acids, inorganic salts (excluding calcium salts) and hydrophilic organic solvents may be added. By adding such a compound(s), any one or more of the sugar yield, the amount of recovered enzyme and the activity of recovered enzyme can be increased. In particular, in cases where the activity of recovered enzyme is high, the amount of the fresh enzyme to be added upon the reuse of the recovered enzyme can be reduced, which is economically preferred.

The secondary hydrolysis may be performed in the presence of a surfactant, and the surfactant is preferably a nonionic surfactant. This is because, in cases where a cationic surfactant, anionic surfactant or amphoteric surfactant is used, the surfactant promotes deactivation of carbohydrase and has an inhibitory action on the secondary hydrolysis reaction. Further, the activity of the recovered enzyme is also decreased, which is not preferred. On the other hand, with a nonionic surfactant, a high sugar yield efficiency and a high enzyme recovery efficiency can be obtained, so that a nonionic surfactant is preferably used.

The nonionic surfactant is also called the non-ionic surfactant, and is a surfactant whose hydrophilic moiety is constituted by a nonelectrolyte. Specific examples of the nonionic surfactant include polyoxyethylene alkyl ethers, polyoxypropylene block copolymers, polyoxyethylene alkyl allyl ethers, polyoxyethylene fatty acid esters, sorbitan fatty acid esters, polyoxyethylene sorbitan fatty acid esters, polyoxyethylene nonyl phenyl ethers, polyoxyethylene naphthyl ethers, polyoxyethylene octylphenyl ethers, polyoxyethylene alkyl amines, glycerin fatty acid esters and acetylene series polyoxyethylene oxides, and these may be used individually or as a mixture of two or more thereof. The nonionic surfactant is preferably a polyoxypropylene block copolymer. The molecular weight of the polyoxypropylene block copolymer is preferably 500 to 15000.

The nonionic surfactant is preferably added at a concentration of 0.05 to 5% by weight. In cases where the concentration is less than 0.05% by weight, the recovery efficiency of carbohydrase is low, while in cases where the concentration is more than 5% by weight, deactivation of carbohydrase is promoted, which is economically disadvantageous and hence not preferred.

The secondary hydrolysis may be carried out in the presence of an inorganic salt(s), and examples of the inorganic salt(s) which may be used include sodium salts, potassium salts, magnesium salts, sulfuric acid salts, ammonium salts, hydrochloric acid salts, phosphoric acid salts, acetic acid salts and nitric acid salts. Examples of more preferred inorganic salts include sodium chloride, sodium acetate, sodium sulfate, sodium hydrogen sulfate, sodium dihydrogen phosphate, sodium hydrogen phosphate, potassium chloride, dipotassium hydrogen phosphate, ammonium sulfate, magnesium chloride and magnesium sulfate. Among these, sodium chloride, sodium sulfate and sodium hydrogen sulfate, which are sodium salts; and magnesium chloride and magnesium sulfate, which are magnesium salts; are most preferred. By addition of such an inorganic salt(s), the Avicel-degrading activity and the xylan-degrading activity in the recovered enzyme can be increased.

Further, as an alternative to such inorganic salts, sea water may be used. Sea water is an aqueous inorganic salt solution which contains 2.6 to 2.7% sodium chloride, 0.3 to 0.4% magnesium chloride, 0.1 to 0.2% magnesium sulfate and about 0.07% potassium chloride and which occurs in nature in the largest amount. Therefore, sea water may be used as an aqueous inorganic salt solution in the secondary hydrolysis. The pH of sea water is mostly dependent on its salt composition, and generally 8.2 to 8.5. Sea water may be used in the secondary hydrolysis either without changing the pH or after adjusting the pH to an arbitrary value. It is preferred to adjust the pH to a value of 5 to 8.3 in view of enhancement of the cellulase activity of the recovered enzyme. For the adjustment of the pH, a common acid such as sulfuric acid or hydrochloric acid may be used, and the acid is not restricted.

Further, as an alternative to such an inorganic salt(s), ash prepared by subjecting cellulose-containing biomass, a pretreated product of cellulose-containing biomass, the saccharification residue obtained after hydrolysis of cellulose-containing biomass, or the like to boiler combustion may be used. Such ash contains a large amount of potassium salts, and an aqueous inorganic salt solution can be prepared by dissolving the salts in water.

The inorganic salt(s) is/are preferably added at a concentration of 0.05 to 5% by weight. In cases where the concentration is less than 0.05% by weight, the recovery efficiency of carbohydrase is low, while in cases where the concentration is more than 5% by weight, deactivation of carbohydrase is promoted, which is economically disadvantageous and hence not preferred. In cases where sea water is used as the aqueous inorganic salt solution, the dilution rate of the sea water is preferably set at 1/10 to 1.

The secondary hydrolysis may be carried out in the presence of a hydrophilic organic solvent(s). The hydrophilic organic solvent means one having a solubility of not less than 100 g/L in water at 20° C. On the other hand, an organic solvent having a solubility of less than 100 g/L under the above conditions is called a hydrophobic organic solvent. Examples of hydrophobic organic solvents include, but are not limited to, 1-butanol (74 g/L), 1-pentanol (27 g/L), 1-hexanol (5.8 g/L), ethyl acetate (83 g/L), hexane (trace amount) and chloroform (trace amount). Representative examples of the hydrophilic organic solvent include methanol, ethanol, 1-propanol, isopropanol, dimethyl sulfoxide, N,N-dimethylformamide, acetone, acetonitrile, ethylene glycol and glycerin. By adding such a hydrophilic organic solvent, the Avicel-degrading activity of the recovered enzyme can be enhanced, which is preferred.

The above hydrophilic organic solvent(s) is/are preferably added at a concentration of 0.05 to 5% by weight. In cases where the concentration is less than 0.05% by weight, the recovery efficiency of carbohydrase is low, while in cases where the concentration is more than 5% by weight, deactivation of carbohydrase is promoted, which is economically disadvantageous and hence not preferred.

The secondary hydrolysis may be carried out in the presence of an amino acid(s), and examples of the amino acid(s) which may be used include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine, and derivatives thereof. Among these amino acids, alanine, arginine, asparagine, cysteine, glutamine, glutamic acid, glycine, histidine, isoleucine, leucine, lysine, methionine, phenylalanine, proline, serine, threonine, tryptophan and valine, which have high solubility in water, are preferred. Arginine, cysteine, glutamic acid, histidine and lysine, with which recovered enzyme having high Avicel-degrading activity can be obtained, are most preferred.

The above amino acid(s) is/are preferably added at a concentration of 0.05 to 5% by weight. In cases where the concentration is less than 0.05 by weight, the recovery efficiency of carbohydrase is low, while in cases where the concentration is more than 5% by weight, deactivation of carbohydrase is promoted, which is economically disadvantageous and hence not preferred.

The primary sugar liquid and/or secondary sugar liquid is/are filtered through an ultrafiltration membrane, and carbohydrase is separated/recovered from the feed side, and a sugar solution is recovered from the permeate side. The molecular weight cutoff of the ultrafiltration membrane is not restricted as long as it allows permeation of glucose (molecular weight, 180), which is a monosaccharide, and allows blocking of the enzyme. More specifically, the molecular weight cutoff may be 500 to 50000, and the ultrafiltration membrane has a molecular weight cutoff of preferably 5000 to 50000, more preferably 10000 to 30000. Examples of the material which may be used for the functional membrane of the ultrafiltration membrane include polyether sulfone (PES), polysulfone (PS), polyacrylonitrile (PAN), polyvinylidene fluoride (PVDF), regenerated cellulose, cellulose, cellulose ester, sulfonated polysulfone, sulfonated polyether sulfone, polyolefin, polyvinyl alcohol, polymethyl methacrylate and polytetrafluoroethylene. Since regenerated cellulose, cellulose and cellulose ester undergo degradation by cellulase, an ultrafiltration membrane using a synthetic polymer material such as PES or PVDF is preferably used. Examples of the method of filtration through an ultrafiltration membrane include dead-end filtration and cross-flow filtration, and the method is preferably cross-flow filtration in view of suppression of membrane fouling. Examples of the form of the ultrafiltration membrane which may be used as appropriate include the flat membrane, spiral-wound membrane, tubular membrane and hollow fiber membrane. Specific examples of the ultrafiltration membrane include Type G-5, Type G-10, Type G-20, Type G-50, Type PW and Type HWS UF, manufactured by DESAL; HFM-180, HFM-183, HFM-251, HFM-300, HFM-116, HFM-183, HFM-300, HFK-131, HFK-328, MPT-U20, MPS-U20P and MPS-U20S, manufactured by KOCH; SPE1, SPE3, SPE5, SPE10, SPE30, SPV5, SPV50 and SOW30, manufactured by Synder; products of Microza (registered trademark) UF series, manufactured by Asahi Kasei Corporation, having molecular weight cutoffs of 3000 to 100000; and NTR7410 and NTR7450, manufactured by Nitto Denko Corporation.

In cases where a compound(s) such as a nonionic surfactant(s), inorganic salt(s), hydrophilic organic solvent(s), amino acid(s) and/or the like is/are added for the secondary hydrolysis, the secondary sugar liquid, of course, contains these compounds added. Such compounds may have inhibitory actions on the later fermentation step depending on their types and the amounts of addition. In such a case, only the recovered enzyme may be separated/recovered from the secondary sugar liquid using an ultrafiltration membrane and the sugar liquid containing inorganic salts obtained in the permeate side may be treated as a waste liquid.

It is preferred to filter the primary sugar liquid and secondary sugar liquid through an ultrafiltration membrane and to further filter the sugar liquid obtained from the permeate side through a reverse osmosis membrane and/or nanofiltration membrane. The secondary sugar liquid is likely to have a lower sugar concentration compared to the primary sugar liquid because, for example, 1) since the secondary sugar liquid is produced by hydrolysis reaction using only carbohydrase adhered to the solids, the absolute amount of carbohydrase is smaller; and 2) the hydrolysis efficiency of lignocellulose which has remained as solids is low. Therefore, in cases where only the secondary sugar liquid, or a mixture of the secondary sugar liquid and the primary sugar liquid is used in the later fermentation step, the concentration of the fermentation product may become low due to low sugar concentration. However, by filtering the sugar liquid through a reverse osmosis membrane and/or nanofiltration membrane, the decrease in the sugar concentration in the sugar liquid can be prevented. The sugar concentration herein means the total amount of monosaccharide components, especially glucose and xylose. The concentration rate in such sugar concentration is not restricted as long as the concentration is carried out to achieve a concentration appropriate for the later fermentation step. The sugar concentration in the sugar solution before the concentration is not restricted, and is preferably 10 g/L to 100 g/L. The sugar concentration after the concentration is not restricted, and the sugar liquid can be generally preferably used in the later fermentation step in cases where the sugar concentration is 50 g/L to 200 g/L.

Examples of the material of the nanofiltration membrane or reverse osmosis membrane include polymer materials such as cellulose acetate polymers, polyamides, polyesters, polyimides, vinyl polymers and polysulfones. The membrane is not restricted to a membrane constituted by only one of the materials, and may be a membrane comprising a plurality of membrane materials.

As the nanofiltration membrane to be used, a spiral-wound membrane element is preferred. Specific examples of the preferred nanofiltration membrane element include a cellulose acetate nanofiltration membrane element GE Sepa, manufactured by GE Osmonics; nanofiltration membrane elements NF99 and NF99HF, manufactured by Alfa-Laval, which have polyamide functional layers; nanofiltration membrane elements NF-45, NF-90, NF-200, NF-270 and NF-400, manufactured by FilmTec Corporation, which have cross-linked piperazine polyamide functional layers; and nanofiltration membrane elements SU-210, SU-220, SU-600 and SU-610, manufactured by Toray Industries, Inc., comprising a nanofiltration membrane UTC60, manufactured by the same manufacturer, which comprises a cross-linked piperazine polyamide as a major component. The nanofiltration membrane element is more preferably NF99 or NF99HF; NF-45, NF-90, NF-200 or NF-400; or SU-210, SU-220, SU-600 or SU-610. The nanofiltration membrane element is still more preferably SU-210, SU-220, SU-600 or SU-610.

As the reverse osmosis membrane, a spiral-wound membrane element is preferred as in the case of the nanofiltration membrane. Specific examples of the preferred reverse osmosis membrane element include polyamide reverse osmosis membrane modules manufactured by TORAY INDUSTRIES, INC. SU-710, SU-720, SU-720F, SU-710L, SU-720L, SU-720LF, SU-720R, SU-710P and SU-720P, which are low-pressure type modules, as well as SU-810, SU-820, SU-820L and SU-820FA containing UTC70 as a reverse osmosis membrane, which are high-pressure type modules; cellulose acetate reverse osmosis membranes manufactured by the same manufacturer SC-L100R, SC-L200R, SC-1100, SC-1200, SC-2100, SC-2200, SC-3100, SC-3200, SC-8100 and SC-8200; NTR-759HR, NTR-729HF, NTR-70SWC, ES10-D, ES20-D, ES20-U, ES15-D, ES15-U and LF10-D, manufactured by Nitto Denko Corporation; RO98pHt, R099, HR98PP and CE4040C-30D, manufactured by Alfa-Laval; GE Sepa, manufactured by GE; and BW30-4040, TW30-4040, XLE-4040, LP-4040, LE-4040, SW30-4040 and SW30HRLE-4040, manufactured by FilmTec Corporation.

The apparatus for carrying out the above-described method for producing a sugar liquid is described below. The apparatus for carrying out the method for producing a sugar liquid needs to comprise as constituents at least: a stirring tank 2 for carrying out the primary hydrolysis; secondary hydrolysis tank 28 or press filtration device 8 for carrying out the secondary hydrolysis; solid-liquid separation device(s) (8, 25, 30) for the primary hydrolysate and the secondary hydrolysate; and ultrafiltration membrane device (12, 33) for separating the carbohydrase and the sugar liquid from the primary sugar liquid and/or the secondary sugar liquid. To describe examples of such an apparatus, specific examples are shown in FIGS. 2 to 8 and FIGS. 10 to 16. The apparatuses in FIGS. 2 to 8 and FIGS. 10 to 16 were classified into Form 1 to Form 4 based on their characteristics. Form 1 is an apparatus form in which the secondary hydrolysis is carried out in a press filtration tank 8, and corresponds to FIGS. 2 to 8.

Form 1 is an example wherein water is circulated into the press filtration chamber, and it is an apparatus form with which the secondary hydrolysis can be carried out as long as the apparatus has a press filtration device 8 for solid-liquid separation. This has an advantage in that the constitution of the apparatus is simple and the cost for the apparatus can hence be suppressed. However, it has a drawback in that the primary sugar liquid and the secondary sugar liquid are contaminated with each other in the apparatus.

Form 2 is an apparatus form comprising a secondary hydrolysis tank 28 for performing the secondary hydrolysis. Form 2 comprises a stirring tank 2 and a secondary hydrolysis tank 28 separately. Form 2 has an advantage in that solids can be resuspended in the secondary hydrolysis tank 28 and the efficiency of the secondary hydrolysis is high. Depending especially on the types and the concentrations of the compounds added for the secondary hydrolysis, the compounds may have inhibitory actions on the later fermentation of a sugar liquid. Therefore, in view of avoiding contamination of the primary sugar liquid and the secondary sugar liquid with each other, it is advantageous to have, as in Form 2, the secondary hydrolysis tank 28 dedicated to the secondary hydrolysis separately from the stirring tank 2 for carrying out the primary hydrolysis, and to further have a solid-liquid separation 30 dedicated to the secondary sugar liquid and an ultrafiltration membrane device 33 dedicated to the secondary sugar liquid. However, Form 2 has a drawback in that, as the total number of equipments including the secondary hydrolysis tank 28 increases, the equipment cost increases.

Form 3, which is an apparatus form wherein the secondary hydrolysis is carried out in the stirring tank 2 in which the primary hydrolysis is also carried out, is shown in a figure. Form 3 is an apparatus form wherein the hydrolysate obtained in the stirring tank 2 is subjected to solid-liquid separation and then returned again to the stirring tank 2, followed by adding water thereto to perform the secondary hydrolysis. Form 3 has an advantage in that the number of equipments can be the smallest and the equipment cost can be reduced. However, Form 3 has a drawback in that the primary sugar liquid and the secondary sugar liquid are contaminated with each other in the apparatus.

Examples of Form 4, which is an example wherein a microfiltration membrane device 36 is placed between a solid-liquid separation device 25 and an ultrafiltration membrane device 12 are partially shown in figures. The placement of the microfiltration membrane device has an advantage in that insoluble microparticles that could not be sufficiently removed by the solid-liquid separation can be removed, and membrane clogging in the ultrafiltration membrane device 12 can be reduced in a later step.

TABLE 1

Figure 10:
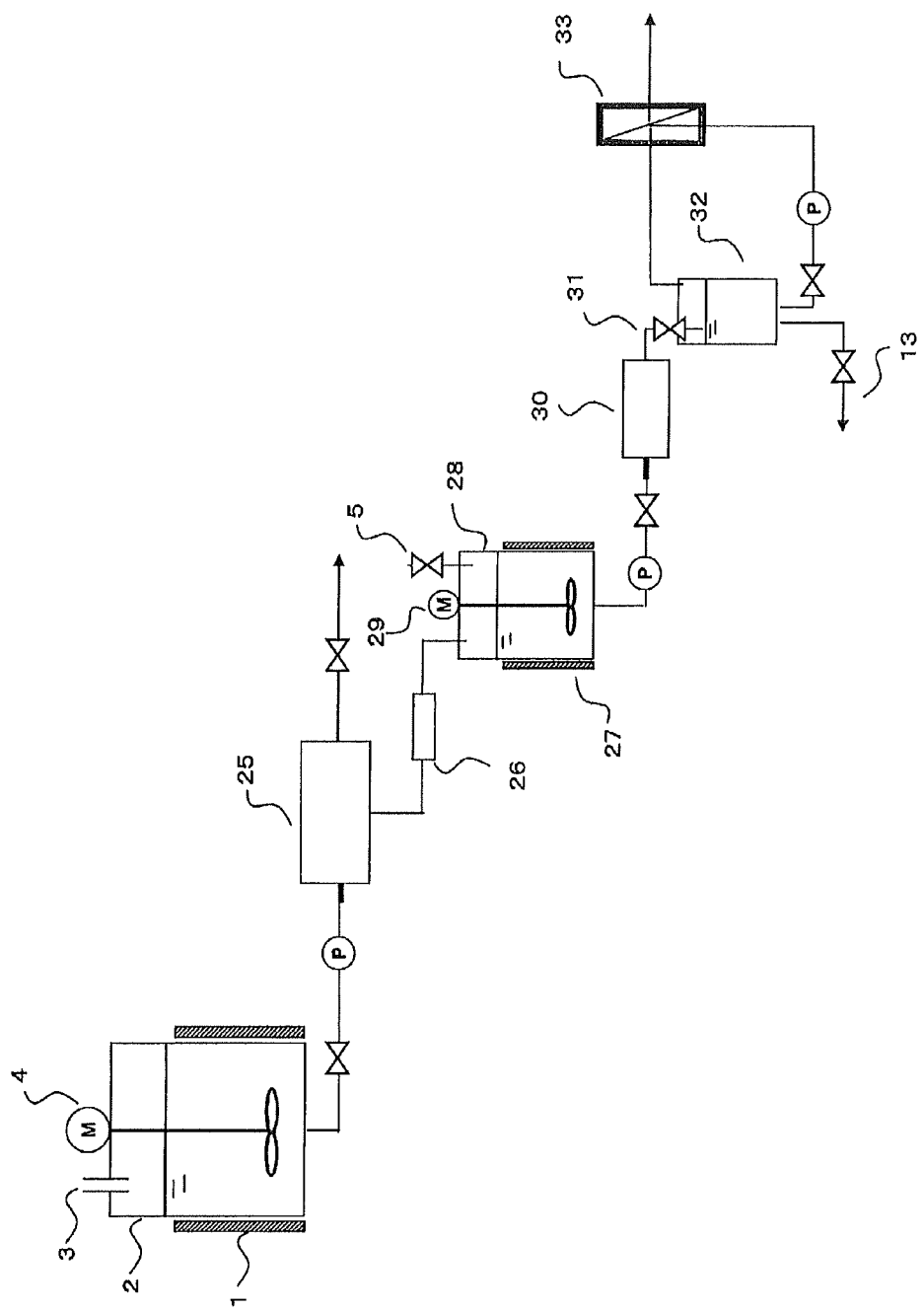
FIG. 10 is a schematic diagram showing an example in which the secondary hydrolysis in the method for producing a sugar liquid is carried out in a secondary hydrolysis tank which is separate from the tank for the primary hydrolysis.
Figure 11:
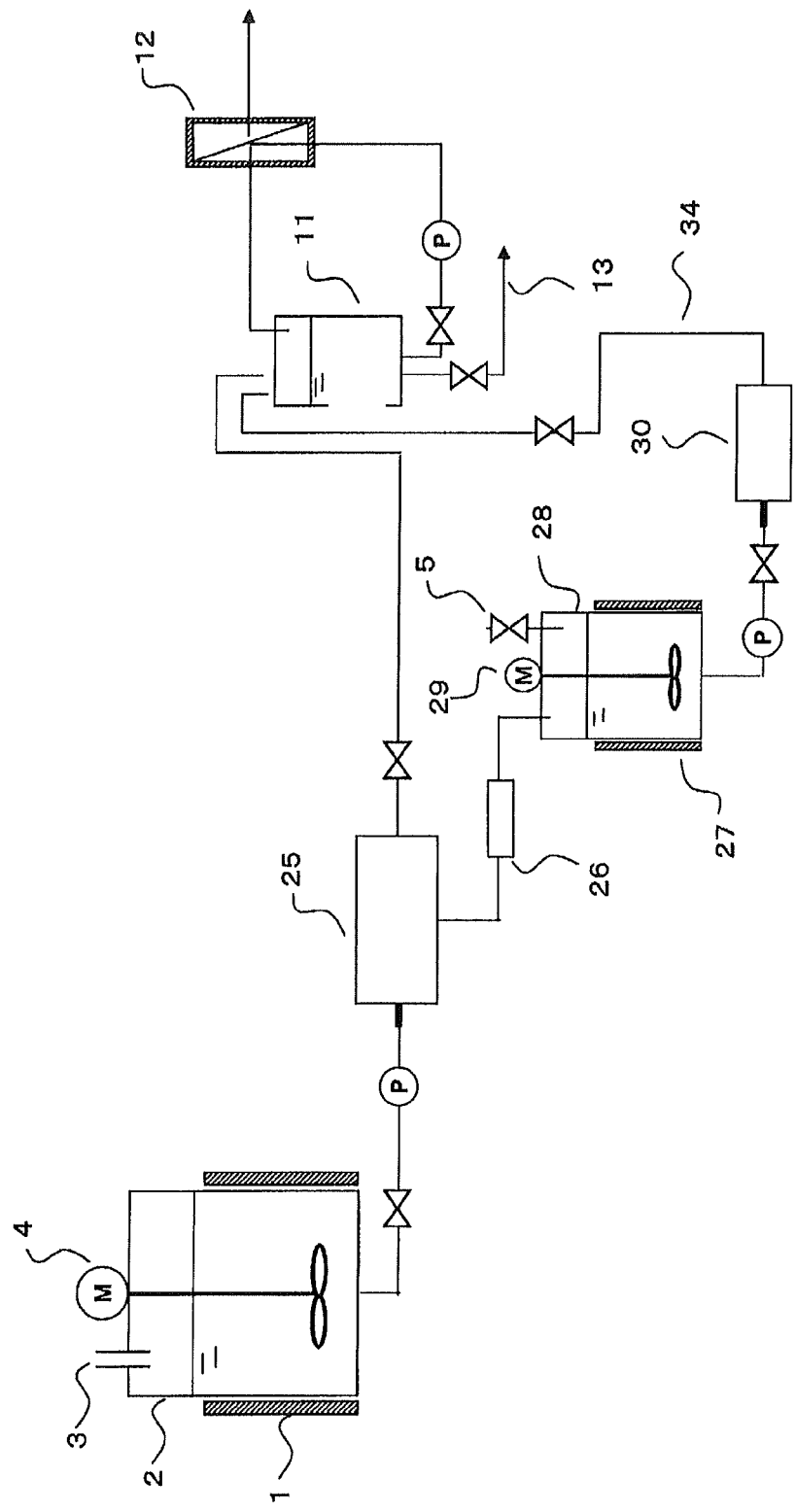
FIG. 11 is a schematic diagram showing an example in which the secondary hydrolysis in the method for producing a sugar liquid is carried out in a secondary hydrolysis tank which is separate from the tank for the primary hydrolysis.
Figure 12:
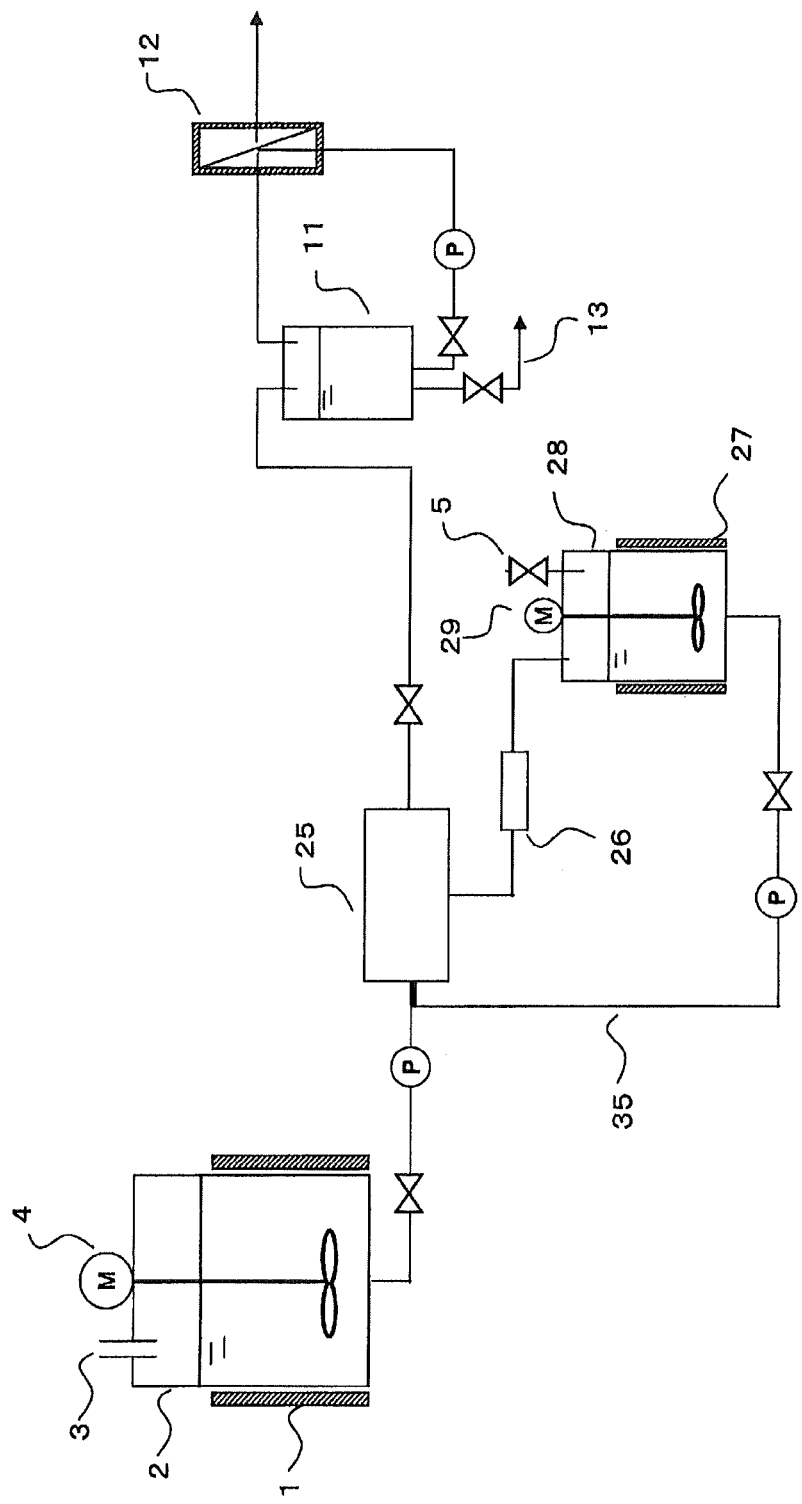
FIG. 12 is a schematic diagram showing an example in which the secondary hydrolysis in the method for producing a sugar liquid is carried out in a secondary hydrolysis tank which is separate from the tank for the primary hydrolysis.
Figure 13:
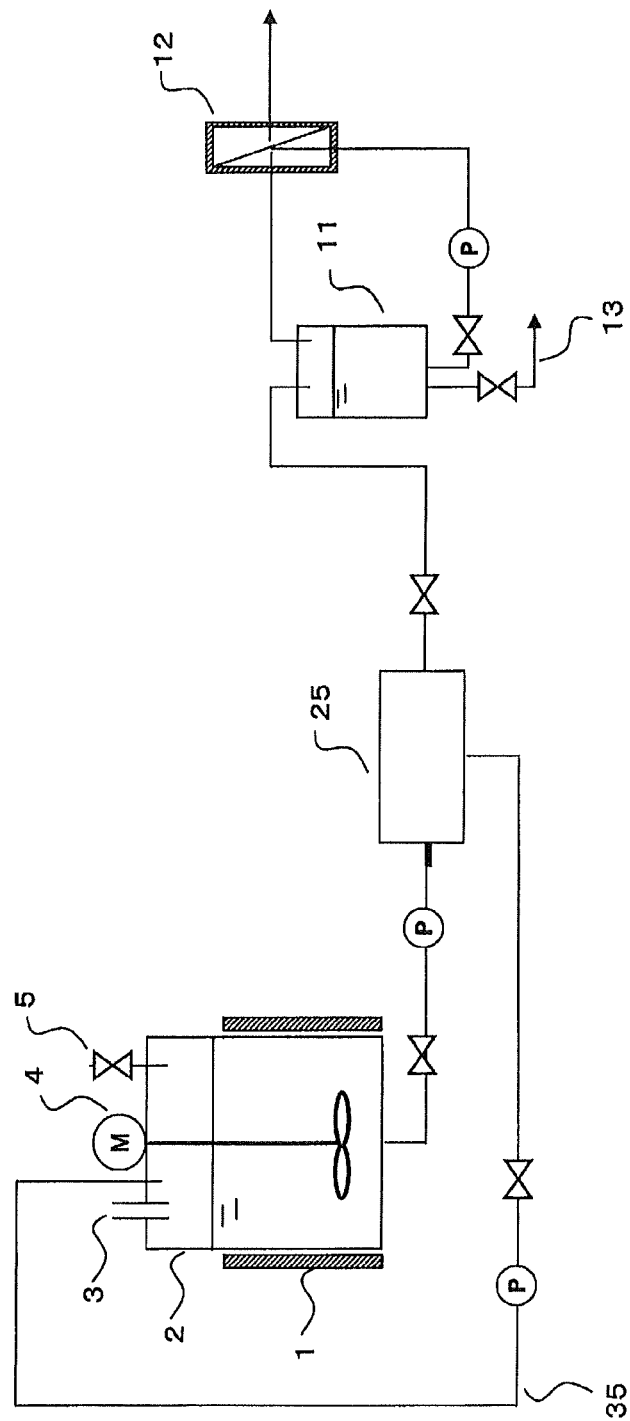
FIG. 13 is a schematic diagram showing an example in which the primary hydrolysis and the secondary hydrolysis in the method for producing a sugar liquid are carried out in the same tank.
Figure 14:
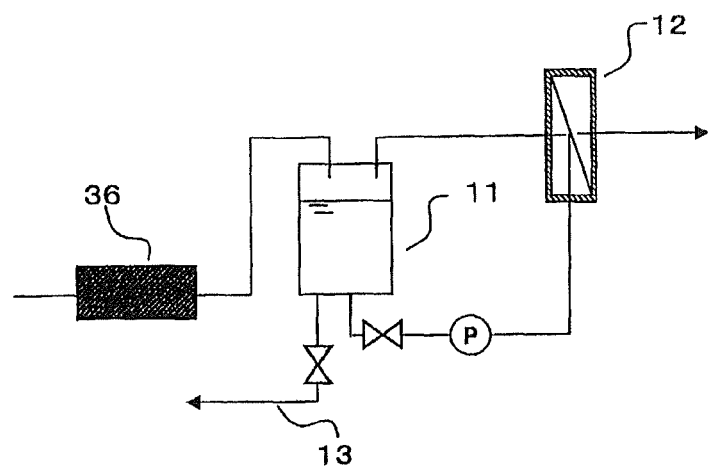
FIG. 14 is a schematic diagram showing an example in which a microfiltration membrane device is placed upstream of an ultrafiltration membrane device.
Figure 15:
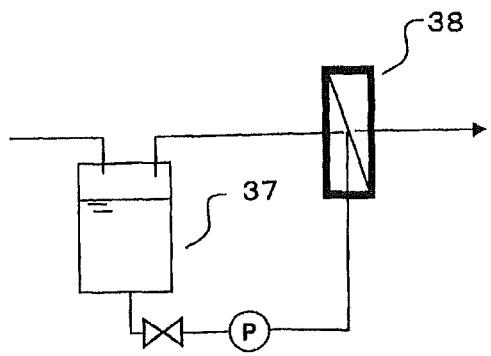
FIG. 15 is a schematic diagram showing an example in which cross-flow filtration is performed using a microfiltration membrane module.
Figure 16:
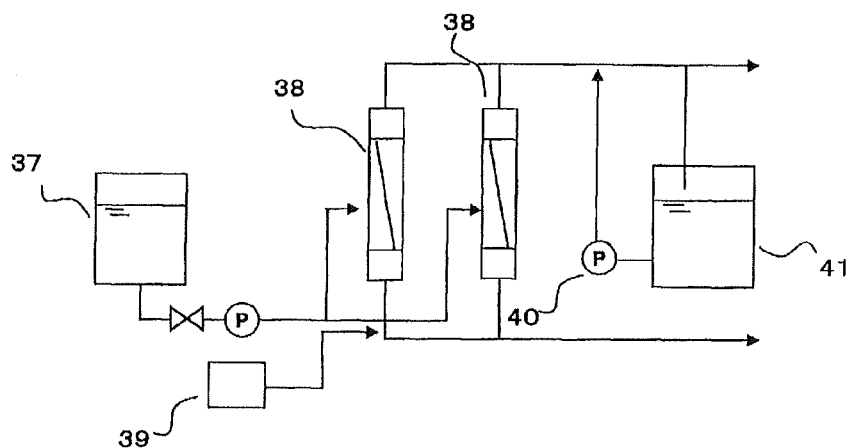
FIG. 16 is a schematic diagram showing an example in which dead-end filtration is performed using a microfiltration membrane module.

| Form | Characteristics of apparatus | Corresponding figures |
|---|---|---|
| 1 | Apparatus form wherein the secondary hydrolysis is carried out in a press filtration tank device | Figs. 2 to 8 |
| 2 | Apparatus form wherein the secondary hydrolysis is carried out in a secondary hydrolysis tank | Figs. 10 to 12 |
| 3 | Apparatus form wherein the secondary hydrolysis is carried out in a stirring tank which is also used for the primary hydrolysis | Fig. 13 |
| 4 | Apparatus form wherein a microfiltration membrane device is placed upstream of an ultrafiltration membrane device (partial diagram) | Figs. 14 to 16 |

Form 1, which is an example wherein the secondary hydrolysis is carried out in a press filtration device, is described below using the schematic diagrams shown in FIGS. 2. to 8.

Examples of the apparatus for carrying out the method for producing a sugar liquid include an apparatus comprising as constituents a stirring tank for the primary hydrolysis 2, press filtration device 8 having a warm-water supply tank 6, circulation line 10 for circulating the filtrate from the press filtration device 8 to the warm-water supply tank 6, and ultrafiltration membrane device 12 for separating the carbohydrase and the sugar solution from the primary sugar liquid and/or the secondary sugar liquid. The apparatus for the method for producing a sugar liquid is described below with reference to the examples of the apparatus shown in figures.

Figure 2:
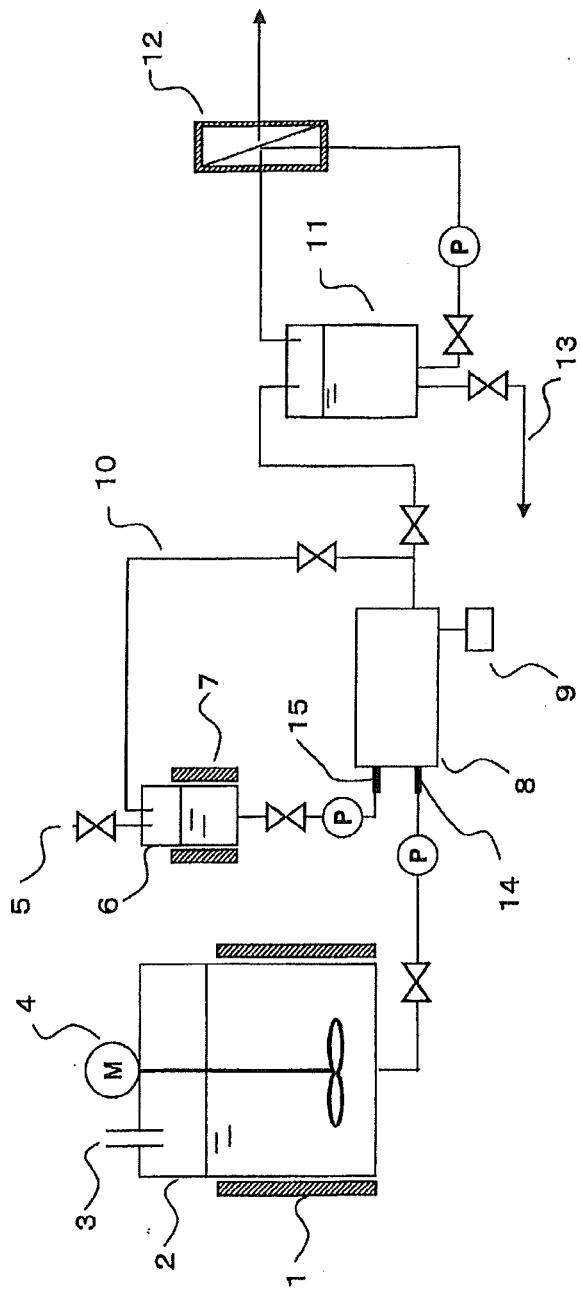
FIG. 2 is a schematic diagram showing an example of our apparatus for carrying out the method for producing a sugar liquid.
Figure 3:
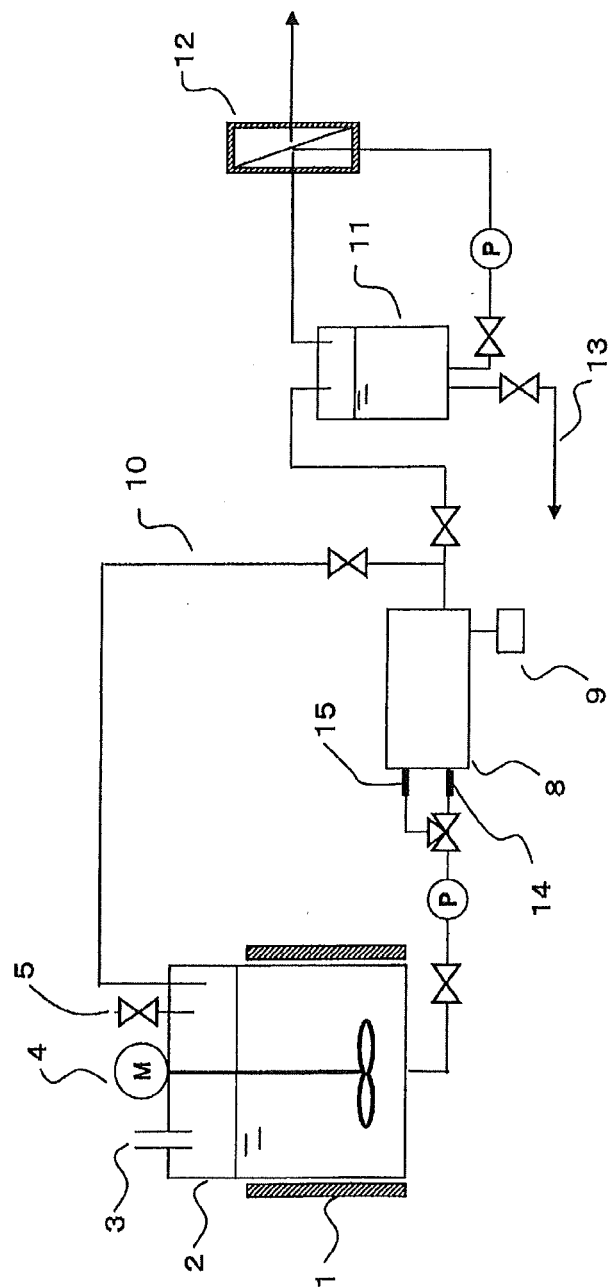
FIG. 3 is a schematic diagram showing an example of our apparatus for carrying out the method for producing a sugar liquid.
Figure 4:
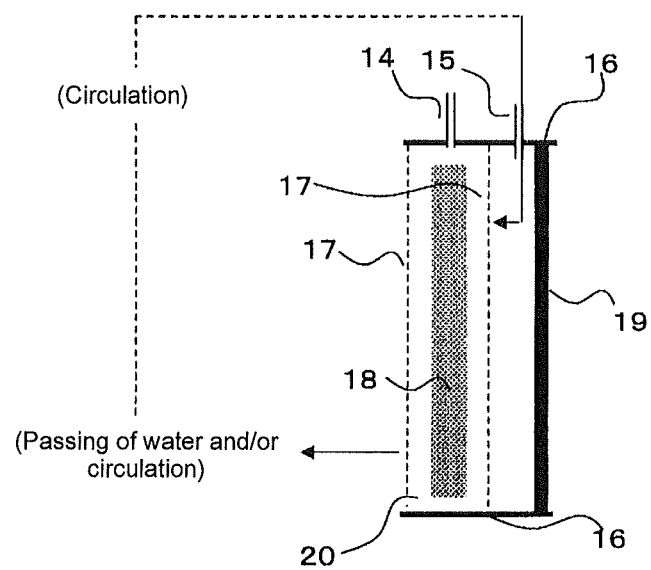
FIG. 4 is a schematic diagram showing an example in which secondary hydrolysis in the method for producing a sugar liquid is carried out in a press filtration chamber.
Figure 5:
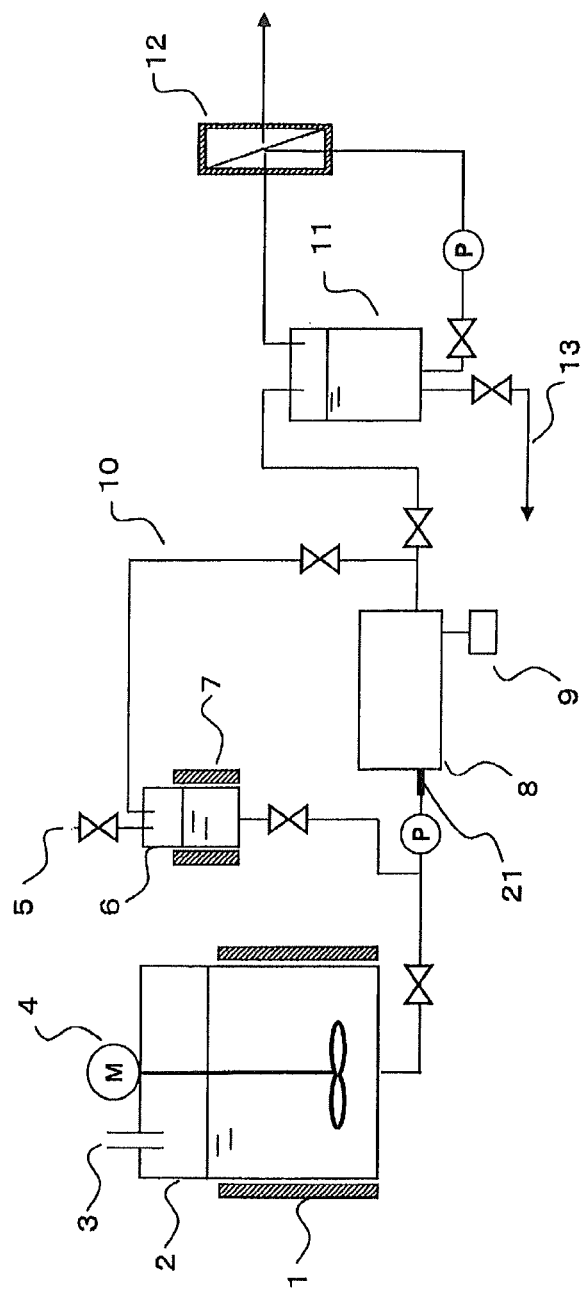
FIG. 5 is a schematic diagram showing an example of the apparatus for carrying out the method for producing a sugar liquid.
Figure 6:
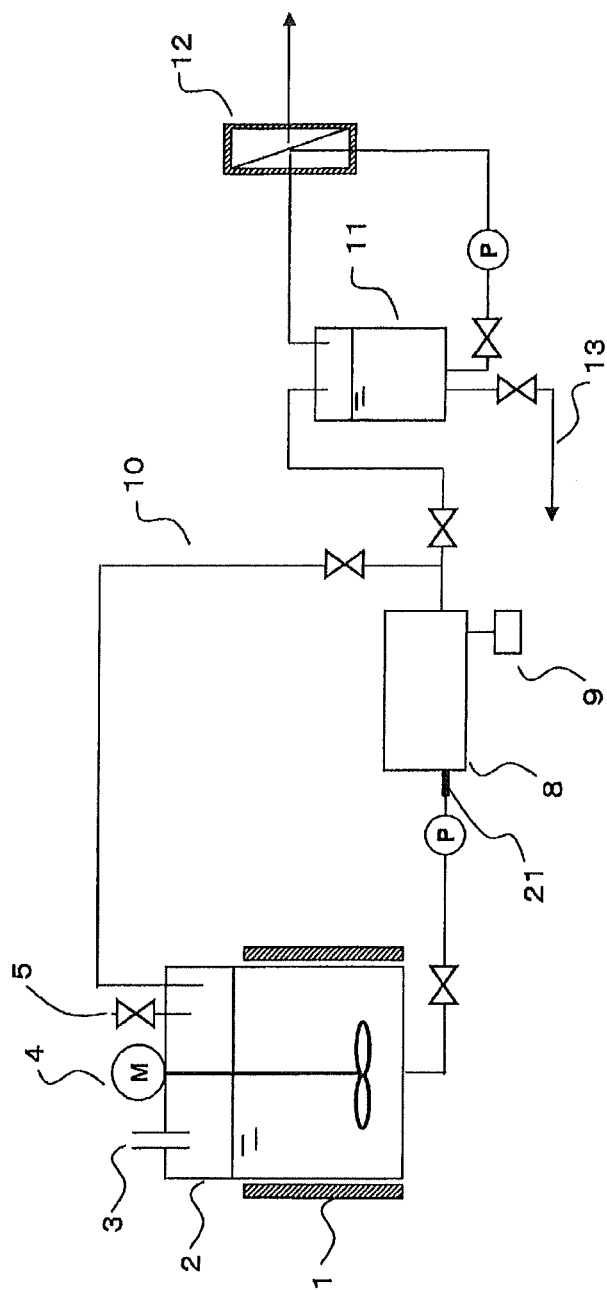
FIG. 6 is a schematic diagram showing an example of the apparatus for carrying out the method for producing a sugar liquid.

FIGS. 2 and 3 are schematic diagrams showing apparatuses each of which uses a press filtration device 8 having a warm-water inlet 15 and a hydrolysate inlet 14 shown in FIG. 4 separately. FIGS. 5 and 6 are schematic diagrams showing apparatuses each of which uses a press filtration device 8 having a hydrolysate-inlet-cum-warm-water inlet 21 shown in FIG. 7. FIGS. 2 and 5 are schematic diagrams showing apparatuses each of which has a stirring tank 2 and a warm-water supply tank 6 separately. On the other hand, FIGS. 3 and 6 are schematic diagrams showing apparatuses each of which uses a stirring tank 2 also as a warm-water supply tank.

The apparatus shown in FIG. 2 is described below in detail. The stirring tank 2 for carrying out the primary hydrolysis has an inlet 3 for supplying cellulose, stirring device 4 for stirring/mixing lignocellulose, and thermostat 1 for keeping the temperature of the stirring tank. The primary hydrolysate obtained in the stirring tank 2 is fed to the press filtration device 8 from a hydrolysate inlet 14. In the press filtration device 8, solid-liquid separation is carried out by compression with a compressor 9, and warm water is supplied from a warm-water supply tank 6 to the solids retained in the press filtration chamber through a warm-water inlet 15. The warm-water supply tank 6 has a water supply line 5, warm-water supply tank thermostat 7 for keeping the temperature of the warm water at a predetermined value, and a circulation line 10 for circulating the filtrate obtained by the press filtration. The primary sugar liquid and/or the secondary sugar liquid obtained by the press filtration is retained in a filtrate recovery tank 11, and filtered through an ultrafiltration membrane device 12. The recovered carbohydrase is recovered and/or reused through a carbohydrase recovery line.

The apparatus shown in FIG. 3 is described below in detail. The stirring tank 2 for carrying out the primary hydrolysis has an inlet 3 for feeding cellulose, stirring device 4 for stirring/mixing cellulose, and thermostat 1 for keeping the temperature of the stirring tank. The primary hydrolysate obtained in the stirring tank 2 is fed to the press filtration device 8 from a hydrolysate inlet 14. In the press filtration device 8, solid-liquid separation is carried out by compression with a compressor 9, and warm water is supplied from a stirring tank 2 to the solids retained in the press filtration chamber through a warm-water inlet 15. A hydrolysate inlet 14 and a warm-water inlet 15 are connected to the press filtration device 8, and the flow can be switched with a valve. The primary sugar liquid and/or the secondary sugar liquid obtained by the press filtration is retained in a filtrate recovery tank 11, and filtered through an ultrafiltration membrane device 12. The recovered carbohydrase is recovered and/or reused through a carbohydrase recovery line.

The apparatus shown in FIG. 5 is described below in detail. The stirring tank 2 for carrying out the primary hydrolysis has an inlet 3 for feeding cellulose, stirring device 4 for stirring/mixing cellulose, and thermostat 1 for keeping the temperature of the stirring tank. The primary hydrolysate obtained in the stirring tank 2 is fed to the press filtration device 8 from a hydrolysate-inlet-cum-warm-water inlet 21. In the press filtration device 8, solid-liquid separation is carried out by compression with a compressor 9, and warm water is supplied from a warm-water supply tank 6 to the solids retained in the press filtration chamber through the hydrolysate-inlet-cum-warm-water inlet 21. The warm-water supply tank 6 has a water supply line 5, warm-water supply tank thermostat 7 for keeping the temperature of the warm water at a predetermined value, and a circulation line 10 for circulating the filtrate obtained by the press filtration. The primary sugar liquid and/or the secondary sugar liquid obtained by the press filtration is/are retained in a filtrate recovery tank 11, and filtered through an ultrafiltration membrane device 12. The recovered carbohydrase is recovered and/or reused through a carbohydrase recovery line.

The apparatus shown in FIG. 6 is described below in detail. The stirring tank 2 for carrying out the primary hydrolysis has an inlet 3 for feeding cellulose, stirring device 4 for stirring/mixing cellulose, and thermostat 1 for keeping the temperature of the stirring tank. The primary hydrolysate obtained in the stirring tank 2 is fed to the press filtration device 8 from a hydrolysate-inlet-cum-warm-water inlet 21. In the press filtration device 8, solid-liquid separation is carried out by compression with a compressor 9, and warm water is supplied from the stirring tank 2 to the solids retained in the press filtration chamber through the hydrolysate-inlet-cum-warm-water inlet 21. The primary sugar liquid and/or the secondary sugar liquid obtained by the press filtration is/are retained in a filtrate recovery tank 11, and filtered through an ultrafiltration membrane device 12. The recovered carbohydrase is recovered and/or reused through a carbohydrase recovery line.

In the above-described apparatuses, the secondary hydrolysis can be carried out by subjecting the primary hydrolysate to press filtration and feeding and/or circulating warm water at 40 to 60° C. to the filtration chamber tank retaining the obtained solids. Since the solids after press filtration have low moisture content and low fluidity, performing the secondary hydrolysis in a separate stirring vessel or the like requires power to supply energy for re-dispersion of the solids. By feeding warm water prewarmed to a temperature within the range of 40 to 60° C. in the warm-water supply tank 6 to the press filtration chamber, the activity of the enzyme components adsorbed to the solids can be increased, so that the secondary hydrolysis can be carried out. In cases where the amount of the warm water fed is too large, the sugar concentration in the secondary sugar liquid is too low, which is not preferred. On the other hand, in cases where the amount of the warm water fed is too small, the reaction temperature in the filtration chamber cannot be sufficiently kept, which is not preferred. It should be noted that, by heating the once-fed water to 40 to 60° C. and circulating the water again, the reaction temperature can be maintained, and the sugar concentration in the secondary sugar liquid can be increased. The length of time of the feeding and/or circulation of warm water is preferably within the range of 5 minutes to 180 minutes. In cases where the length of time is shorter than 5 minutes, the secondary hydrolysis cannot be sufficiently carried out, while in cases where the length of time is longer than 180 minutes, the sugar production rate tends to be saturated, which is not preferred from the viewpoint of energy.

Figure 7:
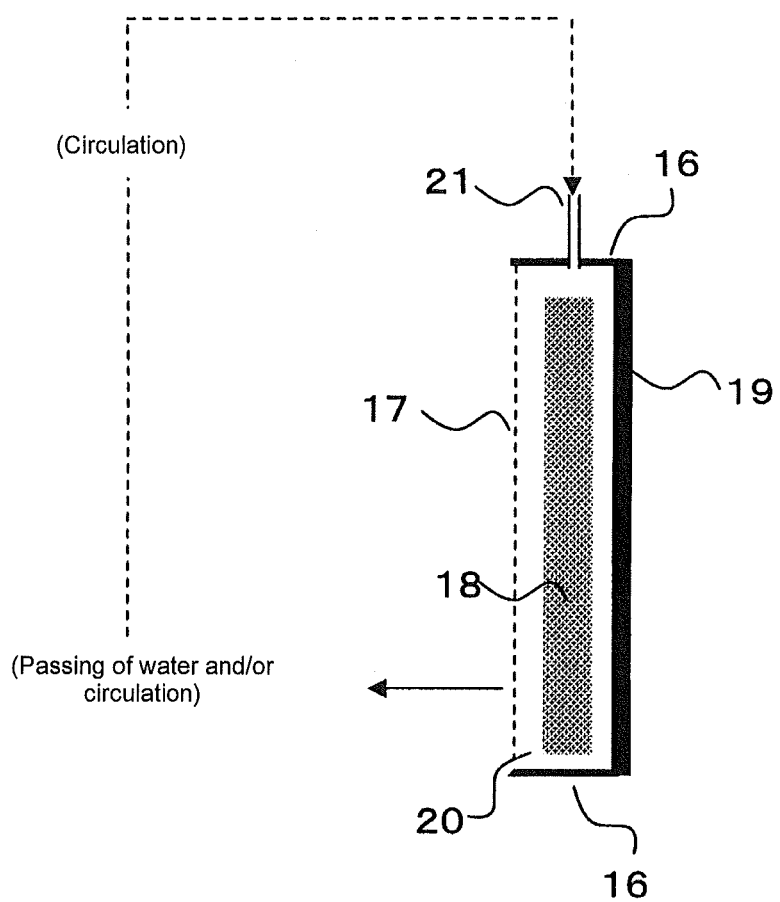
FIG. 7 is a schematic diagram showing an example in which the secondary hydrolysis in the method for producing a sugar liquid is carried out in a press filtration chamber.

The press filtration device is shown in FIGS. 4 and 7 as schematic diagrams. In the device shown in FIG. 4, the primary hydrolysate is fed from the hydrolysate inlet 14 into the press filtration chamber 20, and solid-liquid separation is carried out by compression with a pressing plate 19. Thereafter, warm water is fed through the warm-water inlet 15 to bring the warm water into contact with the solids (primary hydrolysate) 18, followed by being filtered through a filter cloth 17. The filtrate is further circulated through a thermostat, and fed again into the press filtration chamber through the warm-water inlet 15. By allowing such circulation, the secondary hydrolysis can be carried out in the press filtration chamber. FIG. 7 is a schematic diagram showing a method for supplying warm water through a hydrolysate-inlet-cum-warm-water inlet 21. That is, the primary hydrolysate is fed through the hydrolysate-inlet-cum-water inlet 21 into the press filtration chamber 20 and subjected to compression with a pressing plate 19, by which solid-liquid separation is carried out. Thereafter, warm water is fed through the hydrolysate-inlet-cum-warm-water inlet 21 to bring the warm water into contact with the solids (primary hydrolysate) 18, followed by being filtered through a filter cloth 17. The filtrate is further circulated through a thermostat, and fed again into the press filtration chamber through the hydrolysate-inlet-cum-warm-water inlet 21. By allowing such circulation, the secondary hydrolysis can be carried out in the press filtration chamber. The length of time of the feeding and/or circulation of warm water into the press filtration chamber is preferably within the range of 5 minutes to 180 minutes. In cases where the length of time is shorter than 5 minutes, the secondary hydrolysis cannot be sufficiently carried out, while in cases where the length of time is longer than 180 minutes, the sugar production rate tends to be saturated, which is not preferred from the viewpoint of energy. In cases where the amount of the warm water fed is too large, the sugar concentration in the secondary sugar liquid is too low, which is not preferred. On the other hand, in cases where the amount of the warm water fed is too small, the reaction temperature in the filtration chamber cannot be sufficiently kept, which is not preferred. In such cases, by heating the once-fed water to 40 to 60° C. and circulating the water again, the reaction temperature can be maintained, and the sugar concentration in the secondary sugar liquid can be increased.

Figure 8:
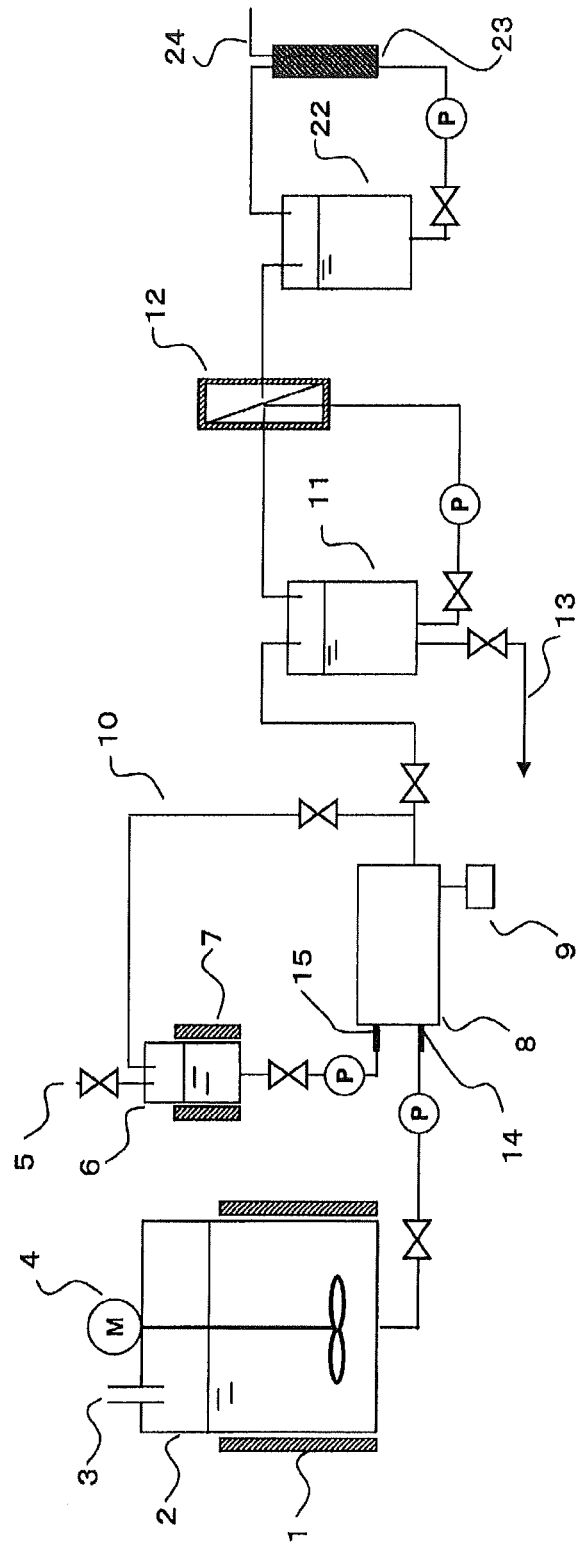
FIG. 8 is a schematic diagram showing an example of the apparatus for carrying out the method for producing a sugar liquid.

FIG. 8 is a schematic diagram showing an apparatus wherein a sugar concentrating device having a reverse osmosis membrane and/or nanofiltration membrane for concentrating the sugar liquid is further attached to the apparatus shown in FIG. 2. More specifically, this apparatus comprises, in the filtrate side of the ultrafiltration membrane device 12, a sugar solution tank 22; nanofiltration membrane device and/or reverse osmosis membrane device 23 connected thereto via a pump; and a filtrate line 24. In cases where the nanofiltration membrane device and/or reverse osmosis membrane device is/are connected to the apparatus shown in FIG. 3, 5 or 6, the nanofiltration membrane device and/or reverse osmosis membrane device may be connected, in the same manner as in FIG. 8, downstream of the ultrafiltration membrane device 12, which is included in the apparatus shown in FIG. 3, 5 or 6 similarly to the apparatus shown in FIG. 2.

Form 2, which is an example wherein the secondary hydrolysis is carried out in a secondary hydrolysis tank, is described below with reference to FIGS. 10 to 12.

FIG. 10 is a diagram showing an example of an apparatus system having a stiffing tank for the primary hydrolysis 2 and a secondary hydrolysis tank 28 separately. The solid-liquid separation device 25 is not restricted as long as it enables solid-liquid separation of the primary hydrolysate using a centrifuge, filter press, belt filter or the like. The solids obtained with the solid-liquid separation device 25 is transferred to the secondary hydrolysis tank 28 by a solid transfer means 26. The solid transfer means 26 is not restricted as long as it is suitable for the properties of the solids, and examples of the means include a belt conveyer and a screw pump. The secondary hydrolysis tank 28 at least comprises a thermostat 2 (secondary hydrolysis tank) 27 for carrying out the secondary hydrolysis. The secondary hydrolysis tank 28 may further comprise a stirring device 2 (secondary hydrolysis tank) 29 for mixing the solids by stirring. The secondary hydrolysis tank 28 further comprises a solid-liquid separation device 2 (secondary hydrolysis tank) 30 for carrying out solid-liquid separation of the secondary hydrolysate. The secondary sugar liquid separated through the solid-liquid separation device 2 (secondary hydrolysis tank) 30 is transferred to a secondary sugar liquid recovery tank 32. The secondary sugar liquid in the secondary sugar liquid recovery tank 32 is filtered through a secondary sugar liquid ultrafiltration membrane device 33 to recover the enzyme.

FIG. 11 shows an example of an apparatus system which has a stirring tank 2 for carrying out the primary hydrolysis and a secondary hydrolysis tank 28 separately, and a solid-liquid separation device 25 and a solid-liquid separation device 2 (secondary hydrolysate) 30 separately, while an ultrafiltration membrane device 12 is shared by the primary sugar liquid and the secondary sugar liquid. As in FIG. 10, the secondary hydrolysate obtained in the secondary hydrolysis tank 28 is subjected to solid-liquid separation in the solid-liquid separation device 2 (secondary hydrolysate) 30, and transferred a filtrate tank 11 through a secondary sugar liquid transfer line 34. The primary sugar liquid and the secondary sugar liquid recovered into the filtrate tank 11 are filtered through an ultrafiltration membrane 12 at once or sequentially, and the enzyme and the sugar are thereby separated.

FIG. 12 shows an example of an apparatus system which has a stirring tank 2 for carrying out the primary hydrolysis and a secondary hydrolysis tank 28 separately, while a solid-liquid separation device 25 and an ultrafiltration membrane device 12 are commonly used by the primary sugar liquid and the secondary sugar liquid. The secondary hydrolysate obtained in a secondary hydrolysis tank 28 is transferred to a solid-liquid separation device 25 through a secondary hydrolysate transfer line 35, and separated into the secondary sugar liquid and solids. The primary sugar liquid and the secondary sugar liquid separated in the solid-liquid separation device 25 is recovered into a filtrate recovery tank 11 and filtered through an ultrafiltration membrane 12 at once or sequentially, and the enzyme and the sugar are thereby separated.

Form 3, which is an example wherein the secondary hydrolysis is carried out in a tank which is also used for the primary hydrolysis, is described below with reference to FIG. 13.

The apparatus shown in FIG. 13 is for an example wherein the primary hydrolysate obtained in a stirring tank 2 for carrying out the primary hydrolysis is separated by a solid-liquid separation device 25, and the obtained solids are circulated to the primary hydrolysis tank through a transfer line 35, followed by carrying out the secondary hydrol-ysis in the primary hydrolysis tank. The primary sugar liquid and the secondary sugar liquid separated in the solid-liquid separation device 25 are collected into a filtrate recovery tank 11, and filtered through an ultrafiltration membrane device 12 to separate the enzyme and the sugar.

Apparatus forms wherein a microfiltration membrane device is placed upstream of an ultrafiltration membrane device are described below with reference to FIGS. 14 to 16. FIG. 14 shows an example (partial diagram) wherein a microfiltration membrane device 36 is placed upstream of an ultrafiltration membrane device 12. The microfiltration membrane device 36 is not restricted as long as it can remove insoluble microparticle components contained in the primary sugar liquid and/or the secondary sugar liquid obtained in the solid-liquid separation device 33 or the press filtration device 8, and examples of the microfiltration membrane device 36 include microfiltration membranes having average pore sizes within the range of 0.01 µm to 1 µm. The method of filtration in the microfiltration membrane device 36 may be either cross-flow filtration (FIG. 15) or dead-end filtration (FIG. 16).

FIG. 15 shows an example of the microfiltration membrane device 36 for performing the microfiltration by cross-flow filtration. The primary sugar liquid and/or the secondary sugar liquid may be stored in a microfiltration membrane raw liquid tank 37 and filtered through a microfiltration membrane 38 while being circulated by a pump.

FIG. 16 shows an example wherein the microfiltration is carried out by dead-end filtration. The primary sugar liquid and/or the secondary sugar liquid is/are stored in a microfiltration membrane raw liquid tank 37 and filtered through a microfiltration membrane 38. In the case of dead-end filtration, a compressed-air supply device 39 for performing air-bubble washing of the membrane surface may be provided as appropriate, and a reverse-washing pump 40 for reverse washing may be placed. The reverse washing may be carried out with the filtrate recovered into a microfiltrate recovery tank 41, or, in some cases, with a common membrane washing liquid or liquid agent. The microfiltration membrane 38 may be in the form of either a flat membrane or hollow fiber membrane. The hollow fiber membrane may be either an internal-pressure type membrane or an external-pressure type membrane.

EXAMPLES

Our methods and apparatus are described below more specifically by way of Examples. However, this disclosure is not restricted to these Examples.

Reference Example 1

Preparation of Pretreated Cellulose

1. Preparation of Pretreated Cellulose 1 (Dilute Sulfuric Acid Treatment)

As the cellulose, rice straw was used. The cellulose was soaked in 1% aqueous sulfuric acid solution, and subjected to treatment using an autoclave (manufactured by Nitto Koatsu Co., Ltd.) at 150° C. for 30 minutes. After the treatment, solid-liquid separation was carried out to separate sulfuric acid-treated cellulose from the aqueous sulfuric acid solution (hereinafter referred to as "dilute-sulfuric-acid treatment liquid"). Subsequently, the sulfuric acid-treated cellulose was mixed with the dilute-sulfuric-acid treatment liquid with stirring such that the concentration of the solid contents is 10% by weight, and the pH was adjusted to about 5 with sodium hydroxide. The resulting mixture was used in the Examples below as the pretreated cellulose 1.

2. Preparation of Pretreated Cellulose 2 (Ammonia Treatment)

As the cellulose, rice straw was used. The cellulose was fed into a compact reactor (manufactured by Taiatsu Techno Corporation, TVS-N2 30 ml), and cooled with liquid nitrogen. Into this reactor, ammonia gas was flown, and the sample was completely soaked in liquid ammonia. The lid of the reactor was closed, and the reactor was left to stand at room temperature for about 15 minutes. Subsequently, the reactor was processed in an oil bath at 150° C. for 1 hour. Thereafter, the reactor was removed from the oil bath, and the ammonia gas was leaked in a fume hood, followed by vacuuming the inside of the reactor to 10 Pa with a vacuum pump, thereby drying the cellulose. The resultant was used in the Examples below as the pretreated cellulose 2.

3. Preparation of Pretreated Cellulose 3 (Hydrothermal Treatment)

As the cellulose, rice straw was used. The cellulose was soaked in water, and subjected to treatment using an autoclave (manufactured by Nitto Koatsu Co., Ltd.) at 180° C. for 20 minutes with stirring. The treatment was carried out at a pressure of 10 MPa. After the treatment, solid-liquid separation was carried out by centrifugation (3000 G) to separate the processed biomass component from the solution component (hereinafter referred to as "hydrothermally treated liquid"). The processed biomass component was used in the Examples below as the pretreated cellulose 3.

Reference Example 2

Measurement of Sugar Concentration

The concentrations of glucose and xylose contained in the sugar liquid were measured under the HPLC conditions described below based on comparison with standard samples:

Column: Luna NH$_2$ (manufactured by Phenomenex, Inc.)
Mobile phase: MilliQ:acetonitrile=25:75 (flow rate, 0.6 mL/minute)
Reaction solution: None
Detection method: RI (differential refractive index)
Temperature: 30° C.

Reference Example 3

Preparation of *Trichoderma*-Derived Cellulase

*Trichoderma*-derived cellulase was prepared by the following method.
Preculture The mixture of 5% corn steep liquor (w/vol), 2% glucose (w/vol), 0.37% ammonium tartrate (w/vol), 0.14% (w/vol) ammonium sulfate, 0.2% (w/vol) potassium dihydrogen phosphate, 0.03% (w/vol) calcium chloride dihydrate, 0.03% (w/vol) magnesium sulfate heptahydrate, 0.02% (w/vol) zinc chloride, 0.01% (w/vol) iron (III) chloride hexahydrate, 0.004% (w/vol) copper (II) sulfate pentahydrate, 0.0008% (w/vol) manganese chloride tetrahydrate, 0.0006% (w/vol) boric acid and 0.0026% (w/vol) hexaammonium heptamolybdate tetrahydrate in distilled water was prepared, and 100 mL of this mixture was placed in a baffled 500-mL Erlenmeyer flask, followed by being sterilized by autoclaving at 121° C. for 15 minutes. After allowing the mixture to cool, PE-M and Tween 80, each of which was sterilized by autoclaving at 121° C. for 15 minutes separately from the mixture, were added thereto at 0.01% (w/vol) each. To this preculture medium, *Trichoderma reesei* PC3-7 was inoculated at 1×10$^5$ cells/mL, and the cells were cultured at 28° C. for 72 hours with shaking at 180 rpm, to perform preculture (shaker: BIO-SHAKER BR-40LF, manufactured by TAITEC CORPORATION).
Main Culture The mixture of 5% corn steep liquor (w/vol), 2% glucose (w/vol), 10% (w/vol) cellulose (Avicel), 0.37% ammonium tartrate (w/vol), 0.14% (w/vol) ammonium sulfate, 0.2% (w/vol) potassium dihydrogen phosphate, 0.03% (w/vol) calcium chloride dihydrate, 0.03% (w/vol) magnesium sulfate heptahydrate, 0.02% (w/vol) zinc chloride, 0.01% (w/vol) iron (III) chloride hexahydrate, 0.004% (w/vol) copper (II) sulfate pentahydrate, 0.0008% (w/vol) manganese chloride tetrahydrate, 0.0006% (w/vol) boric acid and 0.0026% (w/vol) hexaammonium heptamolybdate tetrahydrate in distilled water was prepared, and 2.5 L of this mixture was placed in a 5-L stirring jar (manufactured by ABLE, DPC-2A), followed by being sterilized by autoclaving at 121° C. for 15 minutes. After allowing the mixture to cool, PE-M and Tween 80, each of which was sterilized by autoclaving at 121° C. for 15 minutes separately from the mixture, were added thereto at 0.1% (w/vol) each. To the resulting mixture, 250 mL of preculture of *Trichoderma reesei* PC3-7 preliminarily prepared with a liquid medium by the method described above was inoculated. The cells were cultured at 28° C. for 87 hours at 300 rpm at an aeration rate of 1 vvm. After centrifugation, the supernatant was subjected to membrane filtration (Stericup-GV, manufactured by Millipore, material: PVDF). To the culture liquid prepared under the above-described conditions, β-glucosidase (Novozyme 188) was added at a protein weight ratio of 1/100, and the resulting mixture was used as *Trichoderma*-derived cellulase in the Examples below.

Reference Example 4

Method of Measurement of Cellulase Activity

The cellulase activity was measured and evaluated by the following procedures in terms of four types of degradation activities: 1) Avicel-degrading activity; 2) carboxymethyl cellulose (CMC)-degrading activity; 3) cellobiose-degrading activity; and 4) xylan-degrading activity.

1) Avicel-Degrading Activity

To an enzyme liquid (prepared under predetermined conditions), Avicel (Cellulose Microcrystalline, manufactured by Merck) was added at 1 g/L and sodium acetate buffer (pH 5.0) was added at 100 mM, followed by allowing the resulting mixture to react at 50° C. for 24 hours. This reaction liquid was prepared in a 1-mL tube, and the reaction was allowed to proceed with mixing by rotation under the above-described conditions. Thereafter, the tube was subjected to centrifugation, and the glucose concentration in the supernatant component was measured. The measurement of the glucose concentration was carried out according to the method described in Reference Example 2. The concentration of the produced glucose (g/L) was used as it is as the activity value of the Avicel-degrading activity.

2) CMC-Degrading Activity

To an enzyme liquid, carboxymethyl cellulose was added at 10 g/L and sodium acetate buffer (pH 5.0) was added at 100 mM, followed by allowing the resulting mixture to react at 50° C. for 0.5 hour. This reaction liquid was prepared in a 1-mL tube, and the reaction was allowed to proceed with mixing by rotation under the above-described conditions. Thereafter, the tube was subjected to centrifugation, and the glucose concentration in the supernatant component was measured. The measurement of the glucose concentration was carried out according to the method described in Reference Example 2. The concentration of the produced glucose (g/L) was used as it is as the activity value of the CMC-degrading activity.

3) Cellobiose-Degrading Activity

To an enzyme liquid, cellobiose (Wako Pure Chemical Industries, Ltd.) was added at 500 mg/L and sodium acetate buffer (pH 5.0) was added at 100 mM, followed by allowing the resulting mixture to react at 50° C. for 0.5 hour. This reaction liquid was prepared in a 1-mL tube, and the reaction was allowed to proceed with mixing by rotation under the above-described conditions. Thereafter, the tube was subjected to centrifugation, and the glucose concentration in the supernatant component was measured. The measurement of the glucose concentration was carried out according to the method described in Reference Example 2. The concentration of the produced glucose (g/L) was used as it is as the activity value of the cellobiose-degrading activity.

4) Xylan-Degrading Activity

To an enzyme liquid, xylan (Birch wood xylan, Wako Pure Chemical Industries, Ltd.) was added at 10 g/L and sodium acetate buffer (pH 5.0) was added at 100 mM, followed by allowing the resulting mixture to react at 50° C. for 4 hours. This reaction liquid was prepared in a 1-mL tube, and the reaction was allowed to proceed with mixing by rotation under the above-described conditions. Thereafter, the tube was subjected to centrifugation, and the xylose concentration in the supernatant component was measured. The measurement of the xylose concentration was carried out according to the method described in Reference Example 2. The concentration of the produced xylose (g/L) was used as it is as the activity value of the xylose-degrading activity.

Example 1

Hydrolysis of Cellulose with *Trichoderma*-Derived Cellulase

The results of the primary hydrolysis and the secondary hydrolysis in hydrolysis of cellulose using *Trichoderma*-derived cellulase are described in the Examples below. The method of the experiment was as follows.

(Step 1: Primary Hydrolysis)

To each of the pretreated celluloses 1 to 3 (1 g each), distilled water was added, and 10 mg of *Trichoderma*-derived cellulase was added, followed by adding distilled water such that the total weight is 10 g. Further, dilute sulfuric acid or dilute caustic soda was added thereto to adjust the pH of the composition to a value within the range of 4.5 to 5.3. The composition after the pH adjustment was transferred to a side-arm test tube (φ30 NS14/23, manufactured by Tokyo Rikakikai Co., Ltd.), and the composition was transferred to a side-arm reactor (φ30 NS14/23, manufactured by Tokyo Rikakikai Co., Ltd.), followed by performing hydrolysis at 50° C. for 24 hours with incubation and stirring (compact mechanical stirrer CPS-1000, manufactured by Tokyo Rikakikai Co., Ltd., conversion adapter, feed inlet with a three-way stopcock, incubator MG-2200). The hydrolysate was subjected to solid-liquid separation by centrifugation (3000 G, 10 minutes), and, by this, the hydrolysate was separated into the primary sugar liquid (6 mL) and solids. The glucose and xylose concentrations in the obtained primary sugar liquid were measured by the methods described in Reference Example 2. The sugar yield (mg) in the primary sugar liquid was calculated according to the following equation. Table 2 shows a summary of the results.

Sugar yield (mg) in the primary sugar liquid={sugar concentration (g/L) after 24 hours of incubation−sugar concentration (g/L) after 0 hour of incubation}×6 (mL)

TABLE 2

|  |  | Sugar concentration (g/L) | | | Sugar yield (mg) |
|---|---|---|---|---|---|
|  |  | 0 h | 6 h | 24 h | (24 h, 5 mL) |
| Pretreated cellulose 1 | Glc | 0 | 18 | 36 | 216 |
|  | Xyl | 0 | 6 | 15 | 90 |
| Pretreated cellulose 2 | Glc | 0 | 27 | 46 | 276 |
|  | Xyl | 0 | 6 | 8 | 48 |
| Pretreated cellulose 3 | Glc | 0 | 28 | 35 | 210 |
|  | Xyl | 0 | 4 | 7 | 42 |

(Step 2: Secondary Hydrolysis)

To the solids obtained in Step 1, distilled water was added such that the total weight is 10 g. Further, dilute sulfuric acid or dilute caustic soda was added thereto to adjust the pH of the composition to a value within the range of 4.5 to 5.3. The composition was transferred to a side-arm test tube (φ30 NS14/23, manufactured by Tokyo Rikakikai Co., Ltd.), and the composition was transferred to a side-arm reactor (φ30 NS14/23, manufactured by Tokyo Rikakikai Co., Ltd.), followed by performing the secondary hydrolysis at 50° C. for 1 hour with incubation and stirring (compact mechanical stirrer CPS-1000, manufactured by Tokyo Rikakikai Co., Ltd., conversion adapter, feed inlet with a three-way stopcock, incubator MG-2200). The hydrolysate was subjected to solid-liquid separation by centrifugation (3000 G, 10 minutes), and, by this, the hydrolysate was separated into the secondary sugar liquid (6 mL) and solids. The glucose and xylose concentrations in the obtained secondary sugar liquid were measured by the methods described in Reference Example 2. The sugar yield (mg) in the secondary sugar liquid was calculated according to the following equation:

Sugar yield (mg) in the secondary sugar liquid={sugar concentration (g/L) after 1 hour of incubation−sugar concentration (g/L) after 0 hour of incubation}×6 (mL).

Table 3 shows a summary of the results. It was revealed that, although additional enzyme was not added in the secondary hydrolysis, one hour of incubation caused an increase in the sugar concentration. That is, it was observed that the secondary hydrolysis occurred with only the primary sugar liquid remaining in the solids and/or the enzyme adsorbed to the solids.

TABLE 3

|  |  | Sugar concentration (g/L) | | Sugar yield (mg) |
|---|---|---|---|---|
|  |  | 0 h | 1 h | (1 h, 6 mL) |
| Pretreated cellulose 1 | Glc | 16 | 20 | 24 |
|  | Xyl | 6 | 8 | 12 |
| Pretreated cellulose 2 | Glc | 12 | 16 | 24 |
|  | Xyl | 1 | 2 | 6 |
| Pretreated cellulose 3 | Glc | 11 | 16 | 30 |
|  | Xyl | 1 | 2 | 6 |

(Step 3: Recovery of Carbohydrase)

The primary sugar liquid (6 mL) obtained in the primary hydrolysis in Step 1 and the secondary sugar liquid (6 mL) obtained in the secondary hydrolysis in Step 2 were mixed together, and carbohydrase was recovered from the resulting solution.

The above solution was filtered through an ultrafiltration membrane having a molecular weight cutoff of 10000 (VIVASPIN 20, manufactured by Sartorius stedim biotech, material: PES) by centrifugation at 4500 G until the membrane fraction was reduced to 1 mL. To the membrane fraction, 10 mL of distilled water was added, and the resulting mixture was centrifuged again at 4500 G until the membrane fraction was reduced to 1 mL. Thereafter, the enzyme was recovered from the membrane fraction. The protein concentration of the recovered enzyme was assayed with the BCA measurement kit (BCA Protein Assay Reagent kit, manufactured by PIERCE), using bovine albumin (2 mg/mL) as a standard sample, by measurement of the absorbance at 562 nm to perform colorimetry. The concentration of the enzyme that could be recovered (mg/mL) was multiplied by 1 mL, which was the amount of the solution in the membrane fraction, to calculate the amount of carbohydrase which could be recovered. As a result, as shown in Table 4, it was revealed that the enzyme could be recovered in an amount of 1.6 to 2.6 mg.

TABLE 4

|  | Amount of recovered enzyme (mg) 50° C. |
|---|---|
| Pretreated cellulose 1 | 1.6 |
| Pretreated cellulose 2 | 2.6 |
| Pretreated cellulose 3 | 2.0 |

Example 2

Influences of Reaction Temperature on Sugar Yield/Amount of Recovered Enzyme in Secondary Hydrolysis The secondary hydrolysis was carried out in the same manner as in Step 2 of Example 1 except that the reaction temperature was set within the range of 25° C. to 90° C. The sugar yield (glucose, g) in the secondary sugar liquid (6 mL) was as shown in Table 5. It was revealed that, in the secondary hydrolysis, the sugar yield is highest within the range of 40°

C. to 60° C., that is, at the optimum reaction temperature of *Trichoderma*-derived cellulase.

TABLE 5

|  | 25° C. | 35° C. | 40° C. | 50° C. | 55° C. | 60° C. | 65° C. | 70° C. | 80° C. | 90° C. |
|---|---|---|---|---|---|---|---|---|---|---|
| Pretreated cellulose 1 | 1 | 3 | 20 | 24 | 22 | 15 | 0 | 0 | 0 | 0 |
| Pretreated cellulose 2 | 2 | 3 | 17 | 24 | 20 | 6 | 0 | 0 | 0 | 0 |
| Pretreated cellulose 3 | 0 | 1 | 20 | 30 | 27 | 10 | 0 | 0 | 0 | 0 |

Further, the secondary hydrolysis was carried out in the same manner as in Step 2 of Example 1 except that the reaction temperature was set within the range of 25° C. to 90° C., and the recovery of carbohydrase in Step 3 was carried out, followed by calculating the amount of carbohydrase which could be recovered. As a result, as shown in Table 6, it was revealed that the recovered amount of carbohydrase increases at reaction temperatures within the range of 40 to 60° C. during the secondary hydrolysis. It could be further confirmed that a more preferred temperature during the secondary hydrolysis is 50° C.

TABLE 6

|  | 25° C. | 35° C. | 40° C. | 50° C. | 55° C. | 60° C. | 65° C. | 70° C. | 80° C. | 90° C. |
|---|---|---|---|---|---|---|---|---|---|---|
| Pretreated cellulose 1 | 0 | 0 | 1.0 | 1.6 | 1.4 | 1.4 | 0 | 0 | 0 | 0 |
| Pretreated cellulose 2 | 0 | 0 | 1.6 | 2.6 | 2.1 | 1.3 | 0 | 0 | 0 | 0 |
| Pretreated cellulose 3 | 0 | 0 | 1.4 | 2.0 | 1.5 | 1.3 | 0 | 0 | 0 | 0 |

Example 3

Analysis of Recovered Enzyme

Figure 9:
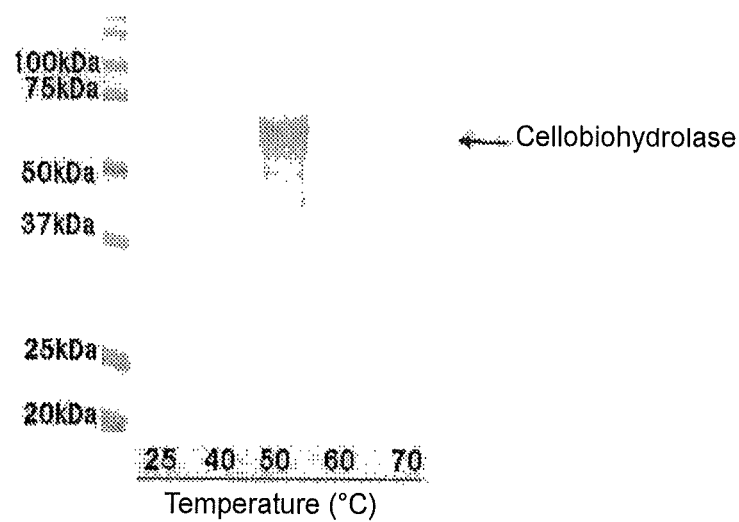
FIG. 9 is a diagram showing the results of analysis of an enzyme contained in the secondary sugar liquid obtained by the method for producing a sugar liquid.

The recovered enzyme obtained in Step 3 of Example 1 (pretreated cellulose 2) was subjected to electrophoresis by SDS-PAGE to analyze recovered enzyme components. First, an equal amount of a sample treatment buffer (Ez Apply, manufactured by ATTO Corporation) was mixed with the recovered enzyme, and the resulting mixture was treated at 100° C. for 10 minutes. To 15% gel for electrophoresis (e-PA-GEL, manufactured by ATTO Corporation), 5 µL of the treated sample was applied, and electrophoresis was carried out (40 mA, 30 minutes). The gel was removed and stained with Coomassie brilliant blue (Bio-safe CBB, manufactured by Bio-Rad Laboratories), followed by decoloration with distilled water. The result obtained by the gel staining after the electrophoresis is shown in FIG. 9. It could be confirmed that, within the range of 40° C. to 60° C., especially cellobiohydrolase among the *Trichoderma*-derived cellulase components is contained as a recovered enzyme component.

Example 4

Relationship Between Reaction Time and Sugar Yield/Amount of Recovered Enzyme in Secondary Hydrolysis The secondary hydrolysis was carried out in the same manner as in Step 2 of Example 1 except that the reaction time was set within the range of 0 to 720 minutes. The sugar yield (glucose, g) in the secondary sugar liquid (6 mL) was as shown in Table 7. It was revealed that a sufficient amount of the sugar can be produced by performing the secondary hydrolysis for not less than 5 minutes. On the other hand, the amount of recovered enzyme did not change within the range exceeding 180 minutes.

TABLE 7

|  | 0 | 1 | 5 | 10 | 30 | 60 | 120 | 180 | 360 | 720 |
|---|---|---|---|---|---|---|---|---|---|---|
| Pretreated cellulose 1 | 0 | 1 | 2 | 6 | 18 | 24 | 30 | 35 | 36 | 36 |
| Pretreated cellulose 2 | 0 | 1 | 4 | 6 | 14 | 24 | 29 | 34 | 34 | 35 |
| Pretreated cellulose 3 | 0 | 1 | 3 | 8 | 20 | 30 | 38 | 42 | 42 | 42 |

Subsequently, the secondary hydrolysis was carried out in the same manner as in Step 2 of Example 1 except that the reaction time was set within the range of 0 to 720 minutes, and the recovery of carbohydrase in Step 3 was carried out, followed by calculating the amount of carbohydrase that could be recovered. As a result, as shown in Table 8, it was revealed that a sufficient amount of the enzyme can be recovered by performing the secondary hydrolysis for not less than 5 minutes. On the other hand, the amount of recovered enzyme did not change within the range exceeding 180 minutes.

TABLE 8

|  | 0 | 1 | 5 | 10 | 30 | 60 | 120 | 180 | 360 | 720 |
|---|---|---|---|---|---|---|---|---|---|---|
| Pretreated cellulose 1 | 0 | 0.1 | 0.3 | 0.5 | 1.2 | 1.6 | 1.9 | 2.4 | 2.4 | 2.6 |
| Pretreated cellulose 2 | 0 | 0.1 | 0.5 | 1.1 | 1.8 | 2.6 | 3.0 | 3.5 | 3.6 | 3.7 |
| Pretreated cellulose 3 | 0 | 0 | 0.5 | 0.8 | 1.5 | 2.0 | 2.4 | 2.8 | 3.0 | 3.1 |

Example 5

Relationship Between pH and Amount of Recovered Enzyme in Secondary Hydrolysis

Step 2 of Example 1 was carried out at 50° C. after adjusting the pH to a value within the range of 4.5 to 5.3 with dilute sulfuric acid or dilute caustic soda. However, in the present Example, the pH was adjusted with dilution buffers to various values within the range of 3 to 10, and the secondary hydrolysis was carried out at 50° C. As a buffer, 2 mM sodium acetate buffer was used for pHs within the range of 3 to 8, while 2 mM glycine-sodium hydroxide buffer was used for pHs within the range of 9 to 10. The experiment was carried out in the same manner as in Example 1 except for the pH adjustment. As a result, as shown in Table 9, it was revealed that the amount of recovered enzyme can be increased by performing the secondary hydrolysis at a pH within the range of 6.0 to 8.0.

TABLE 9

|  | 3 | 4 | 5 | 6 | 7 | 8 | 9 | 10 |
|---|---|---|---|---|---|---|---|---|
| Pretreated cellulose 1 | 0 | 1.2 | 1.6 | 3.0 | 3.4 | 3.4 | 2.0 | 2.0 |
| Pretreated cellulose 2 | 0 | 1.8 | 2.6 | 3.5 | 3.8 | 4.0 | 2.1 | 2.1 |
| Pretreated cellulose 3 | 0 | 1.5 | 2.0 | 3.2 | 3.5 | 3.2 | 1.0 | 1.0 |

Example 6

Relationship Between Amount of Nonionic Surfactant Added and Amount of Recovered Enzyme in Secondary Hydrolysis

As a nonionic surfactant, Pluronic F-68 (manufactured by BASF) was used. The secondary hydrolysis was carried out in the same manner as in Step 2 of Example 1 except that Pluronic F-68 was added such that its final concentration was within the range of 0.01 to 5%. The method was the same as in Example 1 except for the addition of a nonionic surfactant. As a result, as shown in Table 10, the amount of recovered enzyme could be increased by addition of the nonionic surfactant at concentrations within the range of 0.05% to 2%.

TABLE 10

|  | 0.01% | 0.05% | 0.1% | 0.25% | 0.5% | 1% | 2% | 5% |
|---|---|---|---|---|---|---|---|---|
| Pretreated cellulose 1 | 1.6 | 1.8 | 2.1 | 2.3 | 2.5 | 2.9 | 3.3 | 3.3 |
| Pretreated cellulose 2 | 2.7 | 3.0 | 3.2 | 3.6 | 3.8 | 4.1 | 4.2 | 4.2 |
| Pretreated cellulose 3 | 2.0 | 2.1 | 2.4 | 2.6 | 2.9 | 3.4 | 3.7 | 3.8 |

Reference Example 4

Mass Production of Primary Hydrolysate

For mass production of the primary hydrolysate, 20 g of *Trichoderma*-derived cellulase was added to the pretreated cellulose 3 (2 kg), and distilled water was further added such that the total weight is 20 kg. Further, the pH of the composition was adjusted to a value within the range of 4.5 to 5.3 with dilute sulfuric acid or dilute caustic soda. While the liquid was incubated such that a liquid temperature of 45 to 50° C. was maintained, and dilute sulfuric acid and/or dilute caustic soda was/were added to the liquid such that the pH was maintained within the range of 4.5 to 5.3, the enzyme was allowed to react with the pretreated cellulose 3 for 24 hours (the liquid obtained by the reaction is hereinafter referred to as the enzymatic saccharification slurry liquid).

Comparative Example 1

Solid-Liquid Separation by Press Filtration (Solid-Liquid Separation after Primary Hydrolysis)

Using 10 L of the enzymatic saccharification slurry liquid obtained in Reference Example 4, press filtration was carried out by the following procedure. For the press filtration, a compact filter press apparatus (filter press MO-4, manufactured by Yabuta Industries Co., Ltd.) was used. As a filter cloth, a polyester woven fabric (T2731C, manufactured by Yabuta Industries Co., Ltd.) was used. After feeding 10 L of the enzymatic saccharification slurry liquid to the compact tank, the liquid inlet was opened to slowly feeding the enzymatic saccharification slurry liquid to the filtration chamber using an air pump (66053-3EB, manufactured by Taiyo International Corporation) under aeration with compressed air from the bottom. Since the filtrate obtained after 1 minute of the operation remained turbid, the filtrate was returned to the compact tank. The driving pressure of the air pump was gradually increased to increase the pressure in the filtration chamber, and the injection step was continued until filtrate was obtained. The maximum injection pressure at this time was 0.15 MPa. The length of time required for the above injection step was 30 minutes.

Subsequently, a compression step was carried out by swelling the diaphragm attached to the filtration chamber. The compression pressure was gradually increased to 0.5 MPa and the apparatus was then left to stand for about 30 minutes to recover the filtrate. The length of time required for the above compression step was 40 minutes.

After completion of the compression step, the pressure in the diaphragm and the tank was released, and the obtained solids were collected. The total amount of the obtained filtrate was 9.0 L. The remaining liquid component was lost because of the dead volume of the apparatus. Based on the results of measurement of sugar concentrations in the obtained filtrate, that is, the primary sugar liquid of Comparative Example 1, the glucose concentration was 35 g/L and the xylose concentration was 7 g/L. That is, in Comparative Example 1, the glucose yield was 315 g and the xylose yield was 63 g (Table 11).

Comparative Example 2

Solid-Liquid Separation by Press Filtration (Solid-liquid Separation and Washing of Solids after Primary Hydrolysis)

Using 10 L of the enzymatic saccharification slurry liquid obtained in Reference Example 4, press filtration was carried out by the following procedure. The press filtration was carried out using the same apparatus as in Comparative Example 1, and the operating conditions were the same as in Reference Example 1 until the injection step. In the compression step, the compression pressure was increased to 0.2 MPa, and the filtrate was collected for about 5 minutes. The amount of collected filtrate at this time was 8 L. Based on the results of measurement of sugar concentrations in the obtained filtrate, that is, the primary sugar liquid of Comparative Example 2, the glucose concentration was 35 g/L and the xylose concentration was 7 g/L. Therefore, in the primary hydrolysis, the glucose yield (sugar yield in the primary sugar liquid) was 280 g and the xylose yield was 56 g (Table 11).

Subsequently, the solids remaining in the press filtration chamber were washed with water by the following procedure. It should be noted that this operation is not the secondary hydrolysis To the tank, 2.5 L of distilled water at 18° C. was added, and the injection step was carried out at an injection pressure of 0.2 MPa until no filtrate is produced any more. Thereafter, a compression step was carried out by swelling the diaphragm attached to the filtration chamber. The compression pressure was gradually increased to 0.5 MPa and the apparatus was then left to stand for about 30 minutes to recover the filtrate. The length of time required for the above compression step was 35 minutes. After completion of the compression step, the pressure in the diaphragm and the tank was released, and the obtained solids were collected. The total amount of the obtained filtrate was 3.5 L. The remaining liquid component was lost because of the dead volume of the apparatus. Based on the results of measurement of sugar concentrations in the obtained filtrate, that is, the secondary sugar liquid of Comparative Example 2, the glucose concentration was 14 g/L and the xylose concentration was 3.1 g/L. Therefore, the glucose yield was 49 g and the xylose yield was 11 g at this time (Table 11).

TABLE 11

|  |  | Primary hydrolysis (g) | Solid-washing liquid (g) | Total sugar yield (g) |
|---|---|---|---|---|
| Comparative Example 1 | Glc | 315 | 0 | 315 |
|  | Xyl | 63 | 0 | 63 |
| Comparative Example 2 | Glc | 280 | 49 | 329 |
|  | Xyl | 56 | 11 | 67 |

Example 6

Secondary Hydrolysis in Press Filtration Chamber

Using 10 L of the enzymatic saccharification slurry liquid obtained in Reference Example 4, solid-liquid separation and the secondary hydrolysis was carried out by the following procedure.

Press filtration was carried out using the same apparatus as in Comparative Example 2 under the same operating conditions. That is, the amount of filtrate that could be collected was 8 L. Based on the results of measurement of sugar concentrations in the obtained filtrate, that is, the primary sugar liquid of Example 2, the glucose concentration was 35 g/L and the xylose concentration was 7 g/L. Therefore, the glucose yield was 280 g and the xylose yield was 56 g at this time. Table 12 shows a summary of the results as the sugar yield in the primary sugar liquid of Example 6.

Subsequently, the secondary hydrolysis in the press filtration chamber was carried out by the following procedure.

During the compression step, feeding of 2.5 L of distilled water to the tank was started. Thereafter, the tank was heated using a rubber heater until the temperature of the distilled water became 50° C. After the heating, the warm water at 50° C. was fed to the filtration chamber in the same manner as the slurry liquid. The whole obtained filtrate was returned into the tank to allow circulation. This circulation was continued until 1 hour after the beginning of production of the filtrate. Based on the result of measurement of the temperature of the filtrate, the filtrate was at 40° C. after 10 minutes, and was constant at 45° C. after 15 minutes and later. The injection pressure was kept constant at 0.15 MPa. After 120 minutes, the operation of the filtrate side was switched to removal, instead of circulation to the tank. The injection step was continued at an injection pressure of 0.2 MPa until no filtrate was produced any more. Subsequently, a compression step was carried out by swelling the diaphragm attached to the filtration chamber. The compression pressure was gradually increased to 0.5 MPa and the apparatus was then left to stand for about 30 minutes to recover the filtrate. The length of time required for the above compression step was 35 minutes. After completion of the compression step, the pressure in the diaphragm and the tank was released, and the obtained solids were collected. The total amount of the obtained filtrate was 3.5 L. The remaining liquid component was lost because of the dead volume of the apparatus. Based on the results of measurement of sugar concentrations in the obtained filtrate, the glucose concentration was 28 g/L and the xylose concentration was 5 g/L. Therefore, the glucose yield was 98 g and the xylose yield was 17.5 g at this time. Table 12 shows a summary of the results as the sugar yield in the secondary sugar liquid obtained by the secondary hydrolysis and solid-liquid separation in Example 6.

TABLE 12

|  |  | Primary hydrolysis (g) | Secondary hydrolysis (g) | Total sugar yield (g) |
|---|---|---|---|---|
| Example 6 | Glc | 280 | 98 | 378 |
|  | Xyl | 56 | 17.5 | 73.5 |

Comparison of the results of Comparative Example 1 and Comparative Example 2, wherein the secondary hydrolysis was not carried out, with the results of Example 6 shown in Table 12 revealed that the sugar yield can be largely increased by carrying out the secondary hydrolysis.

Example 7

Amount of Recovery of Carbohydrase Obtained by Secondary Hydrolysis in Press Filtration Chamber The primary sugar liquid (6 mL) and the secondary sugar liquid (6 mL) obtained in Example 6 were mixed together, and carbohydrase was recovered from the resulting sugar liquid. For comparison, the primary sugar liquid (6 mL) and the solid-washing liquid (6 mL) obtained in Comparative Example 2 were mixed together, and carbohydrase was also recovered from the resulting sugar liquid. The sugar liquid was filtered through an ultrafiltration membrane having a molecular weight cutoff of 10000 (VIVASPIN 20, manufactured by Sartorius stedim biotech, material: PES) by centrifugation at 4500 G until the membrane fraction was reduced to 1 mL. To the membrane fraction, 10 mL of distilled water was added, and the resulting mixture was centrifuged again at 4500 G until the membrane fraction was reduced to 1 mL. Thereafter, the enzyme was recovered from the membrane fraction. The protein concentration of the recovered enzyme was measured with the BCA measurement kit (BCA Protein Assay Reagent kit, manufactured by PIERCE), using bovine albumin (2 mg/mL) as a standard sample, by measurement of the absorbance at 562 nm to perform colorimetry. The concentration of the enzyme that could be recovered (mg/mL) was multiplied by 1 mL, which was the amount of the solution in the membrane fraction, to calculate the amount of carbohydrase that could be recovered. As a result, as shown in Table 13, it could be confirmed that the amount of recovered carbohydrase is increased by the effect produced by the passing of warm water in Example 6 relative to the amount of the enzyme recovered from the sugar liquid of Comparative Example 2.

TABLE 13

| | Amount of recovered enzyme (mg) 50° C. |
|---|---|
| Comparative Example 2 | 1.6 |
| Example 6 | 3.9 |

Example 8

Recovery and Reuse of Carbohydrase

The primary sugar liquid (8 L) and the secondary sugar liquid (3.5 L) obtained in each of Comparative Example 2 and Example 6 were mixed together, and carbohydrase was recovered from 11.5 L of each of these resulting mixtures. The recovery of carbohydrase was carried out using a compact flat membrane filtration device (Sepa (registered trademark) CF II Med/High Foulant System, manufactured by GE)

equipped with a flat ultrafiltration membrane having a molecular weight cutoff of 10000 (SEPA PW series, manufactured by GE, material of the functional surface: polyether sulfone). While the operating pressure was controlled such that the flow rate in the feed side was constantly 2.5 L/minute and the membrane flux was constantly 0.1 m/D., 11 L out of 11.5 L was filtered. Therefore, 0.5 L of carbohydrase was recovered from the feed side. Subsequently, the obtained recovered enzyme in an amount of 0.5 L was added to the pretreated cellulose 3 (1 kg), and distilled water was further added thereto such that the total weight became 10 kg. Further, dilute sulfuric acid or dilute caustic soda was added thereto to adjust the pH of the composition to a value within the range of 4.5 to 5.3. While the liquid was incubated such that a liquid temperature of 45 to 50° C. was maintained, and dilute sulfuric acid and/or dilute caustic soda was/were added to the liquid such that the pH was maintained within the range of 4.5 to 5.3, the enzyme was allowed to react with the pretreated cellulose 3 for 24 hours. As a result, as shown in Table 14, it could be confirmed that the sugar yield in the case where the enzyme recovered from the sugar liquids (primary and secondary) of Example 6 was used was larger than the sugar yield in the case where the enzyme recovered from the sugar liquids (primary and secondary) of Comparative Example 2 was used.

TABLE 14

| | | Sugar concentration (g/L) 24 h | Sugar yield (mg) (24 h, 6 mL) |
|---|---|---|---|
| Comparative Example 2 | Glc | 10 | 60 |
| | Xyl | 2 | 12 |
| Example 6 | Glc | 27 | 162 |
| | Xyl | 4 | 24 |

Example 9

Concentration of Primary Sugar Liquid and Secondary Sugar Liquid with Reverse Osmosis Membrane (RO Membrane)

Each of the primary sugar liquid and the secondary sugar liquid in Example 6 in an amount of 1 L was concentrated with a reverse osmosis membrane (RO membrane). First, each of the primary sugar liquid and the secondary sugar liquid was prefiltered through a microfiltration membrane having a pore size of 0.45 μm. Each of the obtained membrane-processed liquids in an amount of 1 L was used to perform concentration with an RO membrane. As the RO membrane, a cross-linked entirely aromatic reverse osmosis membrane "UTC80" (manufactured by Toray Industries, Inc.) was used. The RO membrane was mounted on a compact flat membrane filtration device (Sepa (registered trademark) CF II Med/High Foulant System, manufactured by GE), and filtration treatment was carried out at a raw liquid temperature of 25° C. and at a pressure of 3 MPa using a high-pressure pump. By this treatment, 0.7 L of permeate was obtained. The glucose and xylose concentrations at this time were as shown in Table 15, and it could be confirmed that the sugar concentrations in the primary sugar liquid and the secondary sugar liquid can be increased by concentration with an RO membrane.

TABLE 15

| | | Untreated (g/L) | After concentration with an RO membrane (g/L) | Concentration rate (factor) |
|---|---|---|---|---|
| Primary sugar liquid | Glc | 35 | 115 | 3.3 |
| | Xyl | 7 | 23 | 3.3 |
| Secondary sugar liquid | Glc | 28 | 92 | 3.3 |
| | Xyl | 5 | 16 | 3.2 |

Example 10

Concentration of Primary Sugar Liquid and Secondary Sugar Liquid with Nanofiltration Membrane (NF Membrane)

Each of the primary sugar liquid and the secondary sugar liquid in Example 8 in an amount of 1 L was concentrated with a nanofiltration membrane (NF membrane).

First, each of the primary sugar liquid and the secondary sugar liquid was prefiltered through a microfiltration membrane having a pore size of 0.45 μm. Each of the obtained membrane-processed liquids in an amount of 1 L was used to perform concentration with an NF membrane. As the NF membrane, a cross-linked piperazine polyamide nanofiltration membrane "UTC60" (manufactured by Toray Industries, Inc.) was used. The NF membrane was mounted on a compact flat membrane filtration device (Sepa (registered trademark) CF II Med/High Foulant System, manufactured by GE), and filtration treatment was carried out at a raw liquid temperature of 25° C. and at a pressure of 3 MPa using a high-pressure pump. By this treatment, 0.7 L of permeate was obtained. The glucose and xylose concentrations at this time were as shown in Table 16, and it could be confirmed that the sugar concentrations in the primary sugar liquid and the secondary sugar liquid can be increased by concentration with an NF membrane.

TABLE 16

| | | Untreated (g/L) | After concentration with an NF membrane (g/L) | Concentration rate (factor) |
|---|---|---|---|---|
| Primary sugar liquid | Glc | 35 | 112 | 3.2 |
| | Xyl | 7 | 20 | 2.8 |
| Secondary surgar liquid | Glc | 28 | 90 | 3.2 |
| | Xyl | 5 | 14 | 2.8 |

Comparative Example 3

Solid-Liquid Separation by Centrifugation (Solid-Liquid Separation after Primary Hydrolysis)

Using 10 L of the enzymatic saccharification slurry liquid obtained in Example 7, centrifugation was carried out by the following procedure.

To each of 25 500-mL centrifuge tubes, 400 mL of the enzymatic saccharification slurry was fed, and the slurry was subjected to centrifugation at 3000 G for 10 minutes. From each centrifuge tube, 240 mL of the supernatant could be collected, and a total of 6 L of the supernatant could therefore be collected from the 25 centrifuge tubes. The remaining 160 mL (4 L in total) of the content in each centrifuge tube was regarded as the solid in the centrifuge tube and collected. Based on the results of measurement of sugar concentrations in the obtained filtrate, that is, the primary sugar liquid of Example 8, the glucose concentration was 35 g/L and the xylose concentration was 7 g/L. Therefore, in the case where the sugar was obtained by centrifugation for solid-liquid separation, the glucose yield (sugar yield in the primary sugar liquid) was 210 g and the xylose yield was 42 g (Table 17).

Comparative Example 4

Solid-Liquid Separation by Centrifugation (Solid-Liquid Separation and Washing of Solids after Primary Hydrolysis)

Using 10 L of the enzymatic saccharification slurry liquid obtained in Example 7, centrifugation was carried out by the following procedure.

To each of 25 500-mL centrifuge tubes, 400 mL of the enzymatic saccharification slurry was fed, and the slurry was subjected to centrifugation in the same manner as in Comparative Example 3. A total of 6 L of the supernatant could be collected.

The remaining 160 mL (4 L in total) of the content in each centrifuge tube was regarded as the solid in the centrifuge tube and collected. Based on the results of measurement of sugar concentrations in the obtained filtrate, that is, the primary sugar liquid of Example 8, the glucose concentration was 35 g/L and the xylose concentration was 7 g/L. Therefore, in the case where the sugar was obtained by centrifugation for solid-liquid separation, the glucose yield (sugar yield in the primary sugar liquid) was 210 g and the xylose yield was 42 g (Table 17).

Subsequently, the remaining solids were washed with water by the following procedure. It should be noted that this operation is not the secondary hydrolysis.

To the solids collected by centrifugation, water was added, and centrifugation was carried out again to perform solid-liquid separation, thereby collecting the sugar liquid. To the precipitated component in an amount of 160 mL remaining in each of the 25 centrifugation tubes, 100 mL of distilled water was added. The temperature of the distilled water at this time was 18° C. After the addition of water, the centrifuge tubes were lightly rotated for mixing their contents, and centrifuged again at 3000 G for 10 minutes. Thereafter, 150 mL of the supernatant could be collected from each centrifuge tube. That is, a total of 3.75 L of the supernatant could be collected from the 25 centrifuge tubes. Based on the results of measurement of sugar concentrations in the obtained supernatant, that is, the secondary sugar liquid of Comparative Example 4, the glucose concentration was 21 g/L and the xylose concentration was 4 g/L. Therefore, the glucose yield was 79 g and the xylose yield was 15 g at this time (Table 17).

TABLE 17

|  |  | Primary hydrolysis (g) | Solid-washing liquid (g) | Total sugar yield (g) |
|---|---|---|---|---|
| Comparative Example 3 | Glc | 210 | 0 | 210 |
|  | Xyl | 42 | 0 | 42 |
| Comparative Example 4 | Glc | 210 | 79 | 289 |
|  | Xyl | 42 | 15 | 57 |

Example 11

Solid-Liquid Separation by Centrifugation (Primary Hydrolysis and Secondary Hydrolysis)

Using 10 L of the enzymatic saccharification slurry liquid obtained in Reference Example 4, centrifugation was carried out by the following procedure.

To each of 25 500-mL centrifuge tubes, 400 mL of the enzymatic saccharification slurry was fed, and the slurry was subjected to centrifugation in the same manner as in Comparative Example 3. A total of 6 L of the supernatant could be collected.

Subsequently, the secondary hydrolysis of the remaining solids was carried out by the following procedure. To each of 25 500-mL centrifuge tubes, 400 mL of the enzymatic saccharification slurry was fed, and the slurry was subjected to centrifugation at 3000 G for 10 minutes. After the centrifugation, 240 mL of the supernatant could be collected from each centrifuge tube. That is, a total of 6 L of the supernatant could be collected from the 25 centrifuge tubes. The remaining 160 mL (4 L in total) of the content in each centrifuge tube was regarded as the precipitated component in the centrifuge tube and collected. Based on the results of measurement of sugar concentrations in the obtained filtrate, that is, the primary sugar liquid of Example 11, the glucose concentration was 35 g/L and the xylose concentration was 7 g/L. Therefore, in the case where the sugar was obtained by centrifugation for solid-liquid separation, the glucose yield (sugar yield in the primary sugar liquid) was 210 g and the xylose yield was 42 g. These results are summarized in Table 17 as the sugar yield in the case of the primary hydrolysis (sugar yield in the primary sugar liquid).

To the precipitated component collected by the centrifugation, water was added, and centrifugation was carried out again to perform solid-liquid separation, thereby collecting the sugar liquid. To the precipitated component in an amount of 160 mL remaining in each of the 25 centrifugation tubes, 100 mL of distilled water prewarmed to 50° C. was added. Thereafter, the centrifuge tubes were lightly rotated for mixing their contents, and left to stand in an incubator maintained at 50° C. for 1 hour. Subsequently, the centrifuge tubes were lightly rotated for mix-ing their contents, and centrifuged again at 3000 G for 10 minutes. By this, 150 mL of the super-natant could be collected from each centrifuge tube. That is, a total of 3.75 L of the supernatant could be collected from the 25 centrifuge tubes. Based on the results of measurement of sugar concentrations in the obtained supernatant, that is, the secondary sugar liquid of Example 11, the glucose concentration was 29 g/L and the xylose concentration was 5 g/L. Therefore, the glucose yield was 109 g and the xylose yield was 19 g at this time (Table 18).

TABLE 18

|  |  | Primary hydrolysis (g) | Secondary hydrolysis (g) | Total sugar yield (g) |
|---|---|---|---|---|
| Example 11 | Glc | 210 | 109 | 319 |
|  | Xyl | 42 | 19 | 61 |

Based on comparison of the results of Comparative Example 3 and Comparative Example 4 shown in Table 17, wherein the secondary hydrolysis was not carried out, with the results of Example 11 shown in Table 18, it was revealed that the sugar yield can be largely increased by carrying out the secondary hydrolysis. However, based on comparison of the results of Example 11 with the results of Example 6, wherein the solid-liquid separation was carried out by press filtration, it was revealed that the sugar yield is lower in cases where the liquid separation is carried out by centrifugation, as can be seen by comparison between Table 12 and Table 18. This is mainly because higher recovery efficiency of sugar by solid-liquid separation can be achieved by press filtration than by centrifugation.

Example 12

Cellulose-Degrading Activity of Recovered Enzyme in Secondary

Hydrolysis The secondary hydrolysis was carried out under the conditions of Example 1 (pre-treated cellulose 3, 50° C.), Example 2 (pretreated cellulose 3, 25° C.) and Example 5 (pretreated cellulose 3, Pluronic F68: 0.1%, 0.25%, 0.5%, 1%, 2%), and the cellulase activity of each re-covered enzyme was measured by the method in Reference Example 4. Table 19 shows a sum-mary of the activity values represented as relative values calculated using as a standard the activ-ity of the enzyme recovered after the secondary hydrolysis under the conditions of Example 1 (50° C.) (activ-ity=1). The xylan-degrading activity could not be detected for some conditions, and was represented as ND (not detected) in such cases. Since the xylan-degrading activity was ND also for Example 1, which was to be used as the standard, the xylan-degrading activity observed with Pluronic F68: 0.5% for Example 5 was defined as 1 for describing the relative activities.

TABLE 19

| Conditions | | pH | Avicel-degrading activity | CMC-degrading Activity | Cellobiose-degrading activity | Xylan-degrading activity |
|---|---|---|---|---|---|---|
| Example 1 (50° C.) | | 5.0 | 1 | 1 | 1 | ND |
| Example 2 (25° C.) | | 5.0 | ND | ND | ND | ND |
| Example 5 (50° C., Pluronic F-68) | 0.1% | 5.0 | 1.8 | 1.2 | 1.2 | ND |
| | 0.25% | 5.0 | 1.9 | 1.4 | 1.5 | ND |
| | 0.5% | 5.0 | 2.3 | 1.4 | 1.5 | 1 |
| | 1% | 5.0 | 3.0 | 1.4 | 1.7 | 1.3 |
| | 2% | 5.0 | 3.2 | 1.5 | 1.9 | 1.5 |

No cellulase activity was observed for the recovered enzyme for the conditions at 25° C. (Example 2). On the other hand, all the cellulase activities were higher in the recovered enzymes for the conditions at 50° C., especially at 50° C. in the presence of the nonionic surfactant (Pluronic F-68) (Example 5).

Comparative Example 5

Additive Effects on Recovery of Enzyme Using Cationic and Anionic Surfactants

As a compound to be added for the secondary hydrolysis, sodium lauryl sulfate (SDS), which is an anionic surfactant, or 1% benzalkonium chloride, which is a cationic surfactant, was used. The secondary hydrolysis was carried out in the same manner as in Example 1 (pretreated cellulose 3) except that the surfactant was added such that its final concentration was 1%. The recovered enzyme was obtained by the same procedure as in Example 1 and the cellulase activity of the recovered enzyme was measured, but the activity could not be detected for either of the conditions. Therefore, it could be confirmed that, in order to recover the enzyme while maintaining its activity, neither a cationic surfactant nor an anionic surfactant can be used.

Example 13

Relationship Between Type of Inorganic Salt in Secondary Hydrolysis and Activity of Recovered Enzyme As compounds to be added for the secondary hydrolysis, various inorganic salts (sodium chloride, sodium acetate, sodium sulfate, sodium hydrogen sulfate, sodium dihydrogen phosphate, sodium hydrogen phosphate, potassium chloride, ammonium sulfate, magnesium chloride, magnesium sulfate and calcium chloride) were used. The secondary hydrolysis was carried out in the same manner as in Example 1 (pretreated cellulose 3) except that each of the inorganic salts was added such that its final concentration was 1%. The pH after the addition was adjusted with sodium hydroxide or hydrochloric acid to a value within the range of 5.5 to 6.0. The experiment was carried out under the same conditions as in Example 1 (at 50° C., for 1 hour) except for the addition of an inorganic salt. Table 20 shows a summary of the activity values represented as relative values calculated using as a standard the activity of the enzyme recovered after the secondary hydrolysis under the conditions of Example 1 (pretreated cellulose 3, 50° C.) (activity=1). The xylan-degrading activity could not be detected for some conditions, and was represented as ND (not detected) in such cases. Since the xylan-degrading activity was ND also for Example 1, which was to be used as the standard, the xylan-degrading activity observed in the case of dipotassium hydrogen phosphate in Example 5 was defined as 1 for describing the relative activities.

TABLE 20

| Conditions | PH | Avicel-degrading activity | CMC-degrading activity | Cellobiose-degrading activity | Xylan-degrading activity |
|---|---|---|---|---|---|
| Example 1 | 5.0 | 1 (Standard) | 1 (Standard) | 1 (Standard) | ND |
| Sodium chloride | 5.8 | 15 | 3.3 | 2.5 | 3 |
| Sodium acetate | 5.9 | 3.7 | 2.8 | 1.5 | 1.5 |
| Sodium sulfate | 6.0 | 12 | 3.3 | 1.8 | 1.5 |
| Sodium hydrogen sulfate | 6.0 | 11 | 3.0 | 1.4 | 1.1 |
| Sodium dihydrogen phosphate | 5.9 | 4.5 | 3.0 | 1.4 | 1.7 |

TABLE 20-continued

| Conditions | PH | Avicel-degrading activity | CMC-degrading activity | Cellobiose-degrading activity | Xylan-degrading activity |
|---|---|---|---|---|---|
| Sodium hydrogen phosphate | 6.0 | 5 | 3.3 | 1.9 | 2.5 |
| Potassium chloride | 6.1 | 5 | 3.3 | 1.9 | 2.5 |
| Dipotassium hydrogen phosphate | 6.0 | 3 | 2 | 1.4 | 1 (Standard) |
| Ammonium chloride | 6.0 | 7 | 3.3 | 2.2 | 3.3 |
| Magnesium chloride | 5.8 | 30 | 3.3 | 4.3 | 5.5 |
| Magnesium Sulfate | 5.7 | 15 | 3.3 | 2.4 | 5.5 |
| Calcium chloride | 5.6 | ND | ND | ND | ND |
| Calcium sulfate | — | Unperformable | Unperformable | Unperformable | Unperformable |
| Calcium Hydrogen carbonate | — | Unperformable | Unperformable | Unperformable | Unperformable |

As a result, as shown in Table 20, it was revealed that the amount of enzyme recovered tends to be larger in cases where an inorganic salt was added than in cases where no inorganic salt was added. However, it was revealed that the recovered enzyme hardly shows the activities in the case of calcium chloride, which is a calcium inorganic salt. Calcium sulfate and calcium hydrogen carbonate, which are also calcium salts, were studied as well, but the experiment could not be carried out since these could not be dissolved to the predetermined concentration (1%, final concentration) because of their low solubility in water. Therefore, it was revealed that inorganic calcium salts, among inorganic salts, are not suitable as the compound to be added for the secondary hydrolysis.

Example 14

Influence of Concentration of Inorganic Salt Added in Secondary Hydrolysis

The influence of the concentration of the inorganic salt added was confirmed using sodium chloride, which is a sodium salt. By the same procedure as in Example 13, the secondary hydrolysis was carried out at sodium chloride concentrations of 0%, 0.1%, 0.5%, 1% and 5%, and the cellulose-degrading activity of the recovered enzyme was measured similarly to Reference Example 4. Table 21 shows a summary of the activity values represented as relative values calculated using as a standard the activity of the enzyme recovered after the secondary hydrolysis under the conditions of Example 1 (50° C.) (activity=1). The xylan-degrading activity could not be detected for some conditions, and was represented as ND (not detected) in such cases. Since the xylan-degrading activity was ND also for Example 1, which was to be used as the standard, the xylan-degrading activity observed with 0.5% sodium chloride was defined as 1 for describing the relative activities.

TABLE 21

| | Activity | | | |
|---|---|---|---|---|
| Conditions | Avicel-degrading activity | CMC-degrading activity | Cellobiose-degrading activity | Xylan-degrading activity |
| Example 1 | 1 (Standard) | 1 (Standard) | 1 (Standard) | ND |
| 0.1% | 2.8 | 1.3 | 1.5 | ND |
| 0.5% | 7.8 | 2.4 | 1.8 | 1 (Standard) |
| 1% (Example 13) | 15 | 3.3 | 2.5 | 3 |
| 5% | 20 | 4.2 | 2.5 | 8 |

As shown in Table 21, it was revealed that addition of sodium chloride as an inorganic salt at a concentration of even as low as 0.1% increases the Avicel-degrading activity of the recovered enzyme, and addition of sodium chloride at a concentration of not less than 0.5% largely increases all degradation activities compared to the case where sodium chloride was not added.

Example 15

Relationship Between Addition of Inorganic Salt and Secondary Hydrolysis Temperature The secondary hydrolysis was carried out in the presence of 1% sodium chloride at temperatures of 30° C., 40° C., 50° C. and 60° C., and the activity of the recovered enzyme was measured. Table 22 shows a summary of the activity values represented as relative values calculated using as a standard the activity of the enzyme recovered after the secondary hydrolysis under the conditions of Example 1 (pretreated cellulose 3, 50° C.) (activity=1). The xylan-degrading activity could not be detected for some conditions, and was represented as ND (not detected) in such cases. Since the xylan-degrading activity was ND also for Example 1, which was to be used as the standard, the xylan-degrading activity observed with 1% sodium chloride at 60° C. was defined as 1 for describing the relative activities.

TABLE 22

| Conditions | Activity | | | |
|---|---|---|---|---|
| | Avicel-degrading activity | CMC-degrading activity | Cellobiose-degrading activity | Xylan-degrading activity |
| Example 1 | 1 (Standard) | 1 (Standard) | 1 (Standard) | ND |
| 30° C. | 4.4 | 3.0 | 2.0 | 3 |
| 40° C. | 7.4 | 3.3 | 2.1 | 3.2 |
| 50° C. (Example 13) | 15 | 3.3 | 2.5 | 3 |
| 60x: | 2.8 | 3.0 | 2.1 | 1 (Standard) |

As shown in Table 22, it was revealed that, in the presence of sodium chloride, especially the Avicel-degrading activity tends to increase as the temperature becomes closer to 50° C., but the activity rather decreases at 60° C. In terms of the CMC-degrading activity and the cellobiose-degrading activity, no temperature-dependent increase in the amount of recovery could be observed, and the degradation activities did not decrease even at a temperature higher than 60° C. In terms of the xylan-degrading activity, it was revealed that the degradation activity of the recovered enzyme is higher at temperatures within the range of 30° C. to 50° C., but the activity drastically decreases at 60° C.

Example 16

Use of Sea Water as Inorganic Salt in Secondary Hydrolysis

In Examples 13 to 15, it could be confirmed that addition of an inorganic salt can increase the amount and activity of the recovered enzyme. In view of this, a study was performed to see whether "sea water", which is an aqueous solution containing inorganic salts, can be used as an alternative. As the sea water, sea water collected near Misaki fishing port in Kanagawa pref. (pH 8.3; amount of solid dissolved, 3.2%) was used. The pH of the sea water was adjusted with sulfuric acid to pH 6.5 (addition of 24 mg of sulfuric acid per 1 L of sea water), pH 5.0 (addition of 50 mg of sulfuric acid per 1 L of sea water) or pH 3.8 (addition of 100 mg of sulfuric acid per 1 L of sea water). In terms of the amount of the sea water for the secondary hydrolysis, the sea water was added to the solids such that its final concentration was 50% (dilution rate, 1/2). The secondary hydrolysis was carried out at 50° C. for 1 hour. Table 23 shows the activities of the enzyme that could be recovered. The table summarizes the activity values represented as relative values calculated using as a standard the activity of the enzyme recovered after the secondary hydrolysis under the conditions of Example 1 (cellulose, pretreated product 3, 50° C.) (activity=1). The xylan-degrading activity could not be detected for some conditions, and was represented as ND (not detected) in such cases. Since the xylan-degrading activity was ND also for Example 1 (cellulose, pretreated product 3, 50° C.), which was to be used as the standard, the xylan-degrading activity observed in the case of the sea water at pH 3.8 was defined as 1 for describing the relative activities.

TABLE 23

| Conditions | | Activity | | | |
|---|---|---|---|---|---|
| | | Avicel-degrading activity | CMC-degrading activity | Cellobiose-degrading activity | Xylan-degrading activity |
| Example 1 | | 1 (Standard) | 1 (Standard) | 1 (Standard) | ND |
| Sea water | pH 8.3 | 12 | 3.0 | 2.3 | 3 |
| | pH 6.5 | 15 | 3.3 | 2.3 | 3.2 |
| | pH 5.0 | 18 | 3.3 | 2.5 | 3 |
| | pH 3.8 | 2.2 | 2.0 | 2.2 | 1 (Standard) |

As shown in Table 23, it could be confirmed that, also in cases where sea water was used as the inorganic salt, the cellulase activity in the recovered enzyme increases. Further, it was revealed that the degradation activities exhibit similar tendencies to those in cases where a reagent inorganic salt such as sodium chloride was used. However, it was proved that the Avicel-degrading activity is lower at pH 3.8 than at other pHs.

Example 17

Relationship Between Addition of Sea Water and Secondary Hydrolysis Temperature

The secondary hydrolysis was carried out at temperatures of 30° C., 40° C., 50° C. and 60° C. in the presence of the sea water at pH 5.0, which exhibited the highest effect of addition among the sea waters, and the activity of the recovered enzyme was measured. Table 24 shows a summary of the activity values represented as relative values calculated using as a standard the activity of the enzyme recovered after the secondary hydrolysis under the conditions of Example 1 (pretreated cellulose 3, 50° C.) (activity=1). The xylan-degrading activity could not be detected for some conditions, and was represented as ND (not detected) in such cases. Since the xylan-degrading activity was ND also for Example 1 (cellulose, pretreated product 3, 50° C.), which was to be used as the standard, the xylan-degrading activity observed in the case of the sea water at 60° C. was defined as 1 for describing the relative activities.

TABLE 24

| Conditions | Activity | | | |
|---|---|---|---|---|
| | Avicel-degrading activity | CMC-degrading activity | Cellobiose-degrading activity | Xylan-degrading activity |
| Example 1 | 1 (Standard) | 1 (Standard) | 1 (Standard) | ND |
| 30° C. | 4.4 | 3.0 | 2.0 | 3 |
| 40° C. | 7.4 | 3.3 | 2.1 | 3.2 |
| 50° C. (Example 16) | 18 | 3.3 | 3.0 | 3 |
| 60° C. | 2.8 | 3.0 | 2.1 | 1 (Standard) |

As shown in Table 24, it was revealed that, in the presence of sea water, especially the Avicel-degrading activity tends to increase as the temperature becomes closer to 50° C., but the activity rather decreases at 60° C. In terms of the CMC-degrading activity and the cellobiose-degrading activity, no temperature-dependent increase in the amount of recovery could be observed, and the degradation activities did not decrease even at a temperature higher than 60° C. In terms of the xylan-degrading activity, it was revealed that the degradation activity of the recovered enzyme is higher at temperatures within the range of 30° C. to 50° C., but the activity drastically decreases at 60° C. Such tendencies were similar to those observed in Example 15 wherein sodium chloride was used.

Example 18

Relationship Between Amount of Addition of Amino Acid in Secondary Hydrolysis and Amount of Recovered Enzyme As compounds to be added for the secondary hydrolysis, various amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine) were used. The secondary hydrolysis was carried out in the same manner as in Example 1 (pretreated cellulose 3, 50° C.) except that each of the amino acids was added at a final concentration of 1%. Aspartic acid and tyrosine could not be dissolved at the predetermined concentration, and hence the final concentration of 1% could not be achieved. The pH after the addition was adjusted with hydrochloric acid and/or sodium hydroxide to a value within the range of 5.5 to 6.5. The experiment was carried out in the same manner as in Example 1 except for the addition of the amino acid. Table 25 shows a summary of the activity values represented as relative values calculated using as a standard the activity of the enzyme recovered after the secondary hydrolysis under the conditions of Example 1 (cellulose, pretreated product 3, 50° C.) (activity=1). The xylan-degrading activity could not be detected for some conditions, and was represented as ND (not detected) in such cases. Since the xylan-degrading activity was ND also for Example 1 (cellulose, pretreated product 3, 50° C.), which was to be used as the standard, the detectable xylan-degrading activity observed upon use of lysine was defined as 1 for describing the relative activity for histidine.

As a result, as shown in Table 25, it was revealed that addition of the amino acids tends to increase the amount of the recovered enzyme compared to the case where no amino acid was added. Further, it was revealed that, by addition of especially glutamic acid, lysine, histidine, arginine or cysteine among the amino acids, the activity of the recovered enzyme can be increased. It could be confirmed that the effect of addition of cystein is especially high in terms of the Avicel-degrading activity. Further, it could be confirmed that the xylan-degrading activity can be increased especially by addition of lysine or histidine.

Example 19

Relationship Between Addition of Amino Acid and Secondary Hydrolysis Temperature The secondary hydrolysis was carried out at temperatures of 30° C., 40° C., 50° C. and 60° C. in the presence of 1% cystein, which exhibited the highest effect of addition among the amino acids, and the activity of the recovered enzyme was measured. Table 26 shows a summary of the activity values represented as relative values calculated using as a standard the activity of the enzyme recovered after the secondary hydrolysis under the conditions of Example 1 (pretreated cellulose 3, 50° C.) (activity=1). The xylan-degrading activity could not be detected for any of the conditions, and represented as ND (not detected).

TABLE 26

| | Activity | | | |
|---|---|---|---|---|
| Conditions | Avicel-degrading activity | CMC-degrading activity | Cellobiose-degrading activity | Xylan-degrading activity |
| Example 1 | 1 (Standard) | 1 (Standard) | 1 (Standard) | ND |
| 30° C. | 3.4 | 1.2 | 1.2 | ND |
| 40° C. | 6.8 | 1.2 | 1.4 | ND |
| 50° C. (Example 18) | 7.4 | 1.4 | 1.4 | ND |
| 60° C. | 1.5 | 1 | 1 | ND |

TABLE 25

| | | Activity | | | |
|---|---|---|---|---|---|
| Conditions | pH | Avicel-degrading activity | CMC-degrading activity | Cellobiose-degrading activity | Xylan-degrading activity |
| Example 1 | 5.0 | 1 (Standard) | 1 (Standard) | 1 (Standard) | ND |
| Alanine | 6.2 | 1.2 | 1.1 | 1.1 | ND |
| Arginine | 5.6 | 3.7 | 1.3 | 1.3 | ND |
| Asparagine | 5.5 | 1.3 | 1.1 | 1.1 | ND |
| Aspartic acid | — | Unperformable | Unperformable | Unperformable | Unperformable |
| Cysteine | 6.5 | 7.4 | 1.4 | 1.4 | ND |
| Glutamine | 5.4 | 1.2 | 1.1 | 1.1 | ND |
| Glutamic acid | 6.0 | 1.7 | 1.1 | 1.1 | ND |
| Glycine | 6.0 | 1.2 | 1.1 | 1.1 | ND |
| Isoleucine | 6.0 | 3.1 | 1.2 | 1.2 | 1 |
| Isoleucine | 6.0 | 1.2 | 1.1 | 1.1 | ND |
| Leucine | 6.0 | 1.2 | 1.1 | 1.1 | ND |
| Lysine | 5.6 | 3.8 | 1.3 | 1.3 | 1 (Standard) |
| Methionine | 5.8 | 1.2 | 1.1 | 1.1 | ND |
| Phenylalanine | 5.8 | 1.2 | 1.1 | 1.1 | ND |
| Proline | 6.1 | 1.2 | 1.1 | 1.1 | ND |
| Serine | 5.8 | 1.2 | 1.1 | 1.1 | ND |
| Threonine | 5.7 | 1.2 | 1.1 | 1.1 | ND |
| Tryptophan | 5.7 | 1.2 | 1.1 | 1.1 | ND |
| Tyrosine | — | Unperformable | Unperformable | Unperformable | Unperformable |
| Valine | 5.7 | 1.2 | 1.1 | 1.1 | ND |

As shown in Table 26, it was revealed that, in the presence of cysteine, especially the Avicel-degrading activity tends to increase as the temperature becomes closer to 50° C., but the activity rather decreases at 60° C. In terms of the CMC-degrading activity and the cellobiose-degrading activity, no temperature-dependent increase in the amount of recovery could be observed, and the degradation activities did not decrease even at a temperature higher than 60° C. In terms of the xylan-degrading activity, the activity could not be detected for any of the temperatures.

Example 20

Relationship Between Amount of Addition of Hydrophilic Organic Solvent in Secondary Hydrolysis and Activity of Recovered Enzyme As compounds to be added for the secondary hydrolysis, hydrophilic organic solvents (methanol, ethanol, 1-propanol, isopropanol, dimethyl sulfoxide, N,N-dimethylformamide, acetone, acetonitrile, ethylene glycol and glycerin) were used. The secondary hydrolysis was carried out in the same manner as in Example 1 (pretreated cellulose 3, 50° C.) except that each of the hydrophilic organic solvents was added at a final concentration of 1%. The experiment was carried out in the same manner as in Example 1 except for the addition of the hydrophilic organic solvent. Table 27 shows a summary of the activity values represented as relative values calculated using as a standard the activity of the enzyme recovered after the secondary hydrolysis under the conditions of Example 1 (pretreated cellulose 3, 50° C.) (activity=1). The xylan-degrading activity could not be detected for any of the conditions, and represented as ND (not detected).

TABLE 27

| | | Activity | | | |
|---|---|---|---|---|---|
| Conditions | pH | Avicel-degrading activity | CMC-degrading activity | Cellobiose-degrading activity | Xylan-degrading activity |
| Example 1 | 5.0 | 1 (Standard) | 1 (Standard) | 1 (Standard) | ND |
| Methanol | 5.0 | 1.9 | 1.1 | 1.1 | ND |
| Ethanol | 5.0 | 1.9 | 1.1 | 1.1 | ND |
| 1-Propanol | 5.0 | 1.9 | 1.1 | 1.1 | ND |
| Isopropanol | 5.0 | 1.9 | 1.1 | 1.1 | ND |
| Dimethyl sulfoxide | 5.0 | 1.9 | 1.1 | 1.1 | ND |
| N,N-Dimethyl-formamide | 5.0 | 1.9 | 1.1 | 1.1 | ND |
| Acetone | 5.0 | 1.9 | 1.1 | 1.1 | ND |
| Acetonitrile | 5.0 | 1.9 | 1.1 | 1.1 | ND |
| Ethylene glycol | 5.0 | 1.9 | 1.1 | 1.1 | ND |
| Glycerin | 5.0 | 1.9 | 1.1 | 1.1 | ND |

As a result, as shown in Table 27, it was revealed that the activity of the recovered enzyme, especially the Avicel-degrading activity, can be increased by addition of a hydrophilic organic solvent.

Comparative Example 6

Effect of Addition of Hydrophobic Organic Solvent in Secondary Hydrolysis

As compounds to be added for the secondary hydrolysis, n-hexane, 1-butanol and 1-pentanol were used, and the secondary hydrolysis was carried out by the same procedure as in Example 19. However, the hydrophobic organic solvents were separated from the aqueous phase and recovery with the ultrafiltration membrane was difficult. Irrespective of whether the enzyme can be recovered or not, hydrophobic organic solvents were revealed to be unsuitable as compounds to be added for the secondary hydrolysis because they are difficult to handle.

Example 21

Relationship Between Addition of Hydrophilic Organic Solvent and Secondary Hydrolysis Temperature The secondary hydrolysis was carried out at temperatures of 30° C., 40° C., 50° C. (same as in Example 20) and 60° C. in the presence of 1% ethanol, which is one of the hydrophilic organic solvents used in Example 20, and the activity of the recovered enzyme was measured. Table 28 shows a summary of the activity values represented as relative values calculated using as a standard the activity of the enzyme recovered after the secondary hydrolysis under the conditions of Example 1 (pretreated cellulose 3, 50° C.) (activity=1). The xylan-degrading activity could not be detected for any of the conditions, and represented as ND (not detected).

TABLE 28

| | Activity | | | |
|---|---|---|---|---|
| Conditions | Avicel-degrading activity | CMC-degrading activity | Cellobiose-degrading activity | Xylan-degrading activity |
| Example 1 | 1 (Standard) | 1 (Standard) | 1 (Standard) | ND |
| 30° C. | 1.2 | 1.1 | 1.1 | ND |
| 40° C. | 1.7 | 1.1 | 1.1 | ND |
| 50r: (Example 20) | 1.9 | 1.1 | 1.1 | ND |
| 60° C. | 0.6 | 1 | 1.1 | ND |

It was revealed that, in the presence of ethanol, especially the Avicel-degrading activity tends to increase as the temperature becomes closer to 50° C., but the activity rather decreases at 60° C. In terms of the CMC-degrading activity and the cellobiose-degrading activity, no temperature-dependent increase in the amount of recovery could be observed, and the degradation activities did not decrease even at a temperature higher than 60° C. In terms of the xylan-degrading activity, the activity could not be detected for any of the temperatures.

Comparative Example 7

Effect of Addition of Water-Soluble Polymer in Secondary Hydrolysis

As compounds to be added for the secondary hydrolysis, various water-soluble polymers were used. As the water-soluble polymers, polyallylamine-HCl-3S (PAA-3S, Nitto Boseki Co., Ltd.), polyallylamine-HCl-10S (PAA-10S, Nitto Boseki Co., Ltd.), polyethylene glycol #4000 (PEG #4000, Nakalai Tesque), polyethylene glycol #6000 (PEG #6000, Nakalai Tesque), polyethylene glycol #20,000 (PEG #20,000, Wako Pure Chemical Industries, Ltd.), polyvinyl alcohol 500 (PVA, Wako Pure Chemical Industries, Ltd.) and polyvinyl pyrrolidone (PVP, Sigma-Aldrich) were used. The secondary hydrolysis was carried out in the same manner as in Example 1 (cellulose, pretreated product 3, 50° C.) except that each of the water-soluble polymers was added at a final concentration of 1%. The pH after the addition was adjusted with hydrochloric acid and/or sodium hydroxide to a value within the range of 5.5 to 6.5. The experiment was carried out in the same manner as in Example 1 except for the addition of the water-soluble polymer. Table 29 shows a summary of the activity values represented as relative values calculated using as a standard the activity of the enzyme recovered after the secondary hydrolysis under the conditions of Example 1 (cellulose, pretreated product 3, 50° C.) (50° C.) (activity=1). The xylan-degrading activity could not be detected for some conditions, and was represented as ND (not detected) in such cases.

TABLE 29

| | Activity | | | |
|---|---|---|---|---|
| Conditions | Avicel-degrading activity | CMC-degrading activity | Cellobiose-degrading activity | Xylan-degrading activity |
| Example 1 | 1 (Standard) | 1 (Standard) | 1 (Standard) | ND |
| PAA-3S | ND | ND | ND | ND |
| PAA-10S | ND | ND | ND | ND |
| PEG#4000 | 0.4 | 1 | 1 | ND |
| PEG#6000 | 0.6 | 1 | 1 | ND |
| PEG#20,000 | 0.2 | 0.5 | 1 | ND |
| PVA | 0.6 | 1 | 1 | ND |
| PVP | 0.5 | 1 | 1 | ND |

In the presence of the water-soluble polymers, no increase in the activity of the recovered enzyme due to their addition could be observed for any of the degradation activities.

INDUSTRIAL APPLICABILITY

The sugar liquid can be used as a sugar material for various fermentation products.

The invention claimed is:

1. A method of producing a sugar liquid comprising:
   a) adding cellulase having components comprising cellobiohydrase, endoglucanase, exoglucanase, β-glucosidase, xylanase and xylosidase, to cellulose to perform primary hydrolysis and form a primary hydrolysate,
   b) subjecting the primary hydrolysate of step a) to solid-liquid separation into a primary sugar liquid and solids;
   c) adding water without adding cellulose to said solids of step b) and performing secondary hydrolysis on said solids to form a secondary hydrolysate;
   d) subjecting the secondary hydrolysate without addition of cellulose of step c) to solid-liquid separation into a secondary sugar liquid and a residue; and
   e) filtering said primary sugar liquid of step b) and/or secondary sugar liquid of step d) through an ultrafiltration membrane, and recovering said cellulase from the feed side and recovering a sugar liquid from the permeate side.

2. The method according to claim 1, wherein said cellulose is derived from a processed product prepared by ammonia treatment, hydrothermal treatment or dilute sulfuric acid treatment of biomass.

3. The method according to claim 1, wherein said secondary hydrolysis is hydrolysis in the presence of one or more selected from the group consisting of inorganic salts (excluding calcium salts), hydrophilic organic solvents, amino acids and nonionic surfactants, and sugar liquids comprising these substances.

4. The method according to claim 3, wherein said inorganic salt(s) (excluding calcium salts) is/are one or more selected from the group consisting of sodium salts, potassium salts, magnesium salts, sulfuric acid salts, ammonium salts, hydrochloric acid salts, phosphoric acid salts, acetic acid salts and nitric acid salts.

5. The method according to claim 4, wherein said inorganic salt(s) (excluding calcium salts) is/are one or more selected from the group consisting of sodium chloride, sodium acetate, sodium sulfate, sodium hydrogen sulfate, sodium dihydrogen phosphate, sodium hydrogen phosphate, potassium chloride, ammonium chloride, dipotassium hydrogen phosphate, ammonium sulfate, magnesium chloride and magnesium sulfate.

6. The method according to claim 3, wherein said hydrophilic organic solvent(s) is/are one or more selected from the group consisting of methanol, ethanol, 1-propanol, isopropanol, N,N-dimethylformamide, butanol, acetone, acetonitrile, ethylene glycol and glycerin.

7. The method according to claim 3, wherein said amino acid(s) is/are one or more selected from the group consisting of arginine, cysteine, glutamic acid, histidine and lysine.

8. The method according to claim 1, wherein said solid-liquid separation of the primary hydrolysate and/or secondary hydrolysate is carried out by a filter press apparatus.

9. The method according to claim 1, said method further comprising the step of filtering said sugar liquid through a reverse osmosis membrane and/or nanofiltration membrane to concentrate said sugar liquid.

10. The method according to claim 1, wherein said secondary hydrolysis is in a press filtration chamber of filter press apparatus.

11. The method according to claim 10, wherein said secondary hydrolysis is in a press filtration chamber of the filter press apparatus by feeding and/or circulating warm water to the filtration chamber.

12. The method according to claim 10, wherein said secondary hydrolysis is in the press filtration chamber of the press filtration apparatus by feeding and/or circulating warm water at 40 to 60° C. to the filtration chamber within the range of 5 minutes to 180 minutes.

* * * * *